US006652541B1

United States Patent
Vargas et al.

(10) Patent No.: US 6,652,541 B1
(45) Date of Patent: Nov. 25, 2003

(54) METHOD OF SUTURELESS CLOSURE FOR CONNECTING BLOOD VESSELS

(75) Inventors: Jaime Vargas, Palo Alto, CA (US); Stephen A. Yencho, Menlo Park, CA (US); Jamey Nielsen, San Francisco, CA (US); Michael Hendricksen, Menlo Park, CA (US); Bernard A. Hausen, Menlo Park, CA (US)

(73) Assignee: Cardica, Inc, Redwood City, CA (US)

(*) Notice: Subject to any disclaimer, the term of this patent is extended or adjusted under 35 U.S.C. 154(b) by 500 days.

(21) Appl. No.: 09/664,589

(22) Filed: Sep. 18, 2000

Related U.S. Application Data

(62) Division of application No. 09/314,278, filed on May 18, 1999, now Pat. No. 6,428,550.

(51) Int. Cl.[7] .............................................. A61B 17/11
(52) U.S. Cl. ........................ 606/153; 606/151; 623/1.13
(58) Field of Search ................................ 606/151, 153, 606/213, 215, 149, 152, 154, 155; 623/1.1, 1.11, 1.13, 1.31; 128/898

(56) References Cited

U.S. PATENT DOCUMENTS

| | | |
|---|---|---|
| 2,370,776 A | 3/1945 | Carlson |
| 3,254,650 A | 6/1966 | Collito |
| 3,254,651 A | 6/1966 | Collito |
| 3,519,187 A | 7/1970 | Kapitanov et al. |
| 3,774,615 A | 11/1973 | Lim et al. |
| 4,118,806 A | 10/1978 | Porier et al. |
| 4,214,587 A | 7/1980 | Sakura, Jr. |
| 4,217,664 A | 8/1980 | Faso |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |

(List continued on next page.)

FOREIGN PATENT DOCUMENTS

| | | |
|---|---|---|
| DE | 29713335.7 | 11/1997 |
| DE | 19732234 | 1/1999 |
| EP | 0 517 252 | 12/1992 |
| EP | 0 701 800 | 3/1996 |
| EP | 0 885 595 | 12/1998 |
| EP | 0 938 870 | 9/1999 |
| EP | 0 820 724 | 1/2000 |
| EP | 0 820 725 | 1/2000 |
| EP | 0 913 125 | 7/2000 |

(List continued on next page.)

*Primary Examiner*—Michael J. Milano
*Assistant Examiner*—Julian W. Woo
(74) *Attorney, Agent, or Firm*—Brian A. Schar; Wendi L. Weinstein

(57) ABSTRACT

An anastomosis device is a one piece device for connecting a graft vessel to a target vessel without the use of conventional sutures. The anastomosis device includes an expandable tube configured to have a graft vessel secured to the tube. The device has an expandable linkage positioned at one end of the device and expansion of this linkage causes a first radially extending flange to fold outward. This first flange abuts an interior wall of a target vessel and a second flange is formed which abuts an exterior wall of the target vessel trapping the target vessel between the two flanges and secures the end of the graft vessel into an opening in the wall of the target vessel. The device greatly increases the speed with which anastomosis can be performed over known suturing methods and allows anastomosis to be performed in tight spaces.

11 Claims, 24 Drawing Sheets

U.S. PATENT DOCUMENTS

| | | |
|---|---|---|
| 4,503,568 A | 3/1985 | Madras |
| 4,523,592 A | 6/1985 | Daniel |
| 4,534,761 A | 8/1985 | Raible |
| 4,553,542 A | 11/1985 | Schenck et al. |
| 4,577,631 A | 3/1986 | Kreamer |
| 4,589,416 A | 5/1986 | Green |
| 4,593,693 A | 6/1986 | Schenck |
| 4,603,693 A | 8/1986 | Conta et al. |
| 4,607,637 A | 8/1986 | Berggren et al. |
| 4,624,255 A | 11/1986 | Schenck et al. |
| 4,624,257 A | 11/1986 | Berggren et al. |
| 4,657,019 A | 4/1987 | Walsh et al. |
| 4,665,906 A | 5/1987 | Jervis |
| 4,721,109 A | 1/1988 | Healey |
| 4,747,407 A | 5/1988 | Liu et al. |
| 4,752,024 A | 6/1988 | Green et al. |
| 4,773,420 A | 9/1988 | Green |
| 4,861,330 A | 8/1989 | Voss |
| 4,875,815 A | 10/1989 | Phillips, II |
| 4,883,453 A | 11/1989 | Berry et al. |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 5,005,749 A | 4/1991 | Aranyi |
| 5,015,238 A | 5/1991 | Solomon et al. |
| 5,062,842 A | 11/1991 | Tiffany |
| 5,089,006 A | 2/1992 | Stiles |
| 5,104,025 A | 4/1992 | Main et al. |
| 5,119,983 A | 6/1992 | Green et al. |
| 5,129,913 A | 7/1992 | Ruppert |
| 5,156,613 A | 10/1992 | Sawyer |
| 5,156,619 A | 10/1992 | Ehrenfeld |
| 5,171,262 A | 12/1992 | MacGregor |
| 5,178,634 A | 1/1993 | Ramos Martinez |
| 5,187,796 A | 2/1993 | Wang et al. |
| 5,192,289 A | 3/1993 | Jessen |
| 5,193,731 A | 3/1993 | Aranyi |
| 5,205,459 A | 4/1993 | Brinkerhoff et al. |
| 5,211,683 A | 5/1993 | Maginot |
| 5,217,474 A | 6/1993 | Zacca et al. |
| 5,221,281 A | 6/1993 | Klicek |
| 5,222,963 A | 6/1993 | Brinkerhoff et al. |
| 5,234,447 A | 8/1993 | Kaster et al. |
| 5,250,058 A | 10/1993 | Miller et al. |
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Martinez |
| 5,326,205 A | 7/1994 | Anspach, Jr. et al. |
| 5,333,773 A | 8/1994 | Main et al. |
| 5,336,233 A | 8/1994 | Chen |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,401,131 A | 3/1995 | Yoshino |
| 5,443,497 A | 8/1995 | Venbrux |
| 5,447,514 A | 9/1995 | Gerry et al. |
| 5,454,825 A | 10/1995 | Van Leeuwen |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,478,354 A | 12/1995 | Tovey et al. |
| 5,503,635 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| 5,533,661 A | 7/1996 | Main et al. |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough et al. |
| 5,571,167 A | 11/1996 | Maginot |
| 5,643,340 A | 7/1997 | Nunokawa |
| 5,645,520 A | 7/1997 | Nakamura et al. |
| 5,657,429 A | 8/1997 | Wang et al. |
| 5,669,918 A | 9/1997 | Balazs et al. |
| 5,669,934 A | 9/1997 | Sawyer |
| 5,676,670 A | 10/1997 | Kim |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchliffe et al. |
| 5,709,335 A | 1/1998 | Heck |
| 5,709,693 A | 1/1998 | Taylor |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,755,778 A | 5/1998 | Kleshinski |
| 5,762,458 A | 6/1998 | Wang et al. |
| 5,779,718 A | 7/1998 | Green et al. |
| 5,792,135 A | 8/1998 | Madhani et al. |
| 5,797,900 A | 8/1998 | Madhani et al. |
| 5,797,920 A | 8/1998 | Kim |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford, III et al. |
| 5,827,316 A | 10/1998 | Young et al. |
| 5,833,698 A | 11/1998 | Hinchliffe et al. |
| 5,841,950 A | 11/1998 | Wang et al. |
| 5,855,583 A | 1/1999 | Wang et al. |
| 5,868,763 A | 2/1999 | Spence et al. |
| 5,875,782 A | 3/1999 | Ferrari et al. |
| 5,878,193 A | 3/1999 | Wang et al. |
| 5,879,371 A | 3/1999 | Gardiner et al. |
| 5,881,943 A | 3/1999 | Heck et al. |
| 5,893,369 A | 4/1999 | LeMole |
| 5,904,697 A | 5/1999 | Gifford, III et al. |
| 5,907,664 A | 5/1999 | Wang et al. |
| 5,911,036 A | 6/1999 | Wright et al. |
| 5,915,616 A | 6/1999 | Viola et al. |
| 5,921,995 A | 7/1999 | Kleshinski |
| 5,944,730 A | 8/1999 | Nobles et al. |
| 5,947,363 A | 9/1999 | Bolduc et al. |
| 5,957,363 A | 9/1999 | Heck |
| 5,968,089 A | 10/1999 | Krajicek |
| 5,976,159 A | 11/1999 | Bolduc et al. |
| 6,001,124 A | 12/1999 | Bachinski |
| 6,007,544 A | 12/1999 | Kim |
| 6,013,190 A | 1/2000 | Berg et al. |
| 6,015,416 A | 1/2000 | Stefanchik et al. |
| 6,022,367 A | 2/2000 | Sherts |
| 6,024,748 A | 2/2000 | Manzo et al. |
| 6,030,370 A | 2/2000 | Kupka et al. |

| | | | | | | |
|---|---|---|---|---|---|---|
| 6,030,395 A | 2/2000 | Nash et al. | WO | | 98/19634 | 5/1998 |
| 6,036,699 A | 3/2000 | Andreas et al. | WO | | 98/19636 | 5/1998 |
| 6,036,700 A | 3/2000 | Stefanchik et al. | WO | | 98/30153 | 7/1998 |
| 6,036,702 A | 3/2000 | Bachinkski et al. | WO | | 98/37814 | 9/1998 |
| 6,036,703 A | 3/2000 | Evans et al. | WO | | 98/40036 | 9/1998 |
| 6,036,704 A | 3/2000 | Yoon | WO | WO | 98/42262 | 10/1998 |
| 6,036,705 A | 3/2000 | Nash et al. | WO | | 98/47430 | 10/1998 |
| 6,050,472 A | 4/2000 | Shibata | WO | | 98/55027 | 12/1998 |
| 6,053,390 A | 4/2000 | Green et al. | WO | | 99/08603 | 2/1999 |
| 6,056,762 A | 5/2000 | Nash et al. | WO | | 99/11178 | 3/1999 |
| 6,066,144 A | 5/2000 | Wolf et al. | WO | WO | 99/17665 | 4/1999 |
| 6,066,148 A | 5/2000 | Rygaard | WO | WO | 99/18887 | 4/1999 |
| 6,068,637 A | 5/2000 | Popov et al. | WO | WO | 99/21491 | 5/1999 |
| 6,074,416 A * | 6/2000 | Berg et al. ............... 623/1.1 | WO | | 99/37218 | 7/1999 |
| 6,080,167 A | 6/2000 | Lyell | WO | | 99/38441 | 8/1999 |
| 6,080,173 A | 6/2000 | Williamson, IV et al. | WO | WO | 99/38454 | 8/1999 |
| 6,083,234 A | 7/2000 | Nicholas et al. | WO | | 99/40851 | 8/1999 |
| 6,110,188 A | 8/2000 | Narciso, Jr. | WO | | 99/40868 | 8/1999 |
| 6,113,612 A | 9/2000 | Swanson et al. | WO | | 99/45848 | 9/1999 |
| 6,117,148 A | 9/2000 | Ravo et al. | WO | | 99/52481 | 10/1999 |
| 6,120,432 A | 9/2000 | Sullivan et al. | WO | | 99/62406 | 12/1999 |
| 6,146,393 A | 11/2000 | Wakabayashi | WO | | 99/62409 | 12/1999 |
| 6,149,681 A | 11/2000 | Houser et al. | WO | | 99/62415 | 12/1999 |
| 6,152,937 A | 11/2000 | Peterson et al. | WO | | 99/63910 | 12/1999 |
| 6,152,945 A | 11/2000 | Bachinski et al. | WO | | 99/65409 | 12/1999 |
| 6,165,185 A | 12/2000 | Shennib et al. | WO | WO | 00/09040 | 2/2000 |
| 6,167,889 B1 | 1/2001 | Benetti | WO | | 00/10486 | 3/2000 |
| 6,171,319 B1 | 1/2001 | Nobles et al. | WO | | 00/12013 | 3/2000 |
| 6,171,321 B1 | 1/2001 | Gifford, III et al. | WO | | 00/15144 | 3/2000 |
| 6,176,413 B1 | 1/2001 | Heck et al. | WO | | 00/15146 | 3/2000 |
| 6,176,864 B1 | 1/2001 | Chapman | WO | | 00/15147 | 3/2000 |
| 6,186,942 B1 | 2/2001 | Sullivan et al. | WO | | 00/15148 | 3/2000 |
| 6,187,019 B1 | 2/2001 | Stefanchik et al. | WO | | 00/15149 | 3/2000 |
| 6,187,020 B1 | 2/2001 | Zegdi et al. | WO | | 00/27310 | 5/2000 |
| 6,190,396 B1 | 2/2001 | Whitin et al. | WO | | 00/27311 | 5/2000 |
| 6,190,397 B1 | 2/2001 | Spence et al. | WO | | 00/27312 | 5/2000 |
| 6,190,590 B1 | 2/2001 | Randall et al. | WO | | 00/27313 | 5/2000 |
| 6,193,129 B1 | 2/2001 | Bittner et al. | WO | | 00/33745 | 6/2000 |
| 6,193,734 B1 | 2/2001 | Bolduc et al. | WO | | 00/41633 | 7/2000 |
| 6,206,912 B1 | 3/2001 | Goldsteen et al. | WO | | 00/53104 | 9/2000 |
| 6,206,913 B1 | 3/2001 | Yencho et al. | WO | | 00/56223 | 9/2000 |
| 6,235,054 B1 | 5/2001 | Berg et al. | WO | | 00/56226 | 9/2000 |
| 6,461,320 B1 * | 10/2002 | Yencho et al. ............. 623/1.13 | WO | | 00/56227 | 9/2000 |
| 6,485,496 B1 | 11/2002 | Suyker et al. | WO | | 00/56228 | 9/2000 |
| 6,524,322 B1 * | 2/2003 | Berreklouw ................ 606/153 | WO | | 00/59380 | 10/2000 |
| | | | WO | | 00/66007 | 11/2000 |
| | FOREIGN PATENT DOCUMENTS | | WO | | 00/66009 | 11/2000 |
| EP | 0 990 420 | 12/2000 | WO | | 00/69343 | 11/2000 |
| FR | 2316910 | 4/1977 | WO | | 00/69346 | 11/2000 |
| WO | WO 92/08513 | 5/1992 | WO | | 00/69349 | 11/2000 |
| WO | 96-25886 | 8/1996 | WO | | 00/69364 | 11/2000 |
| WO | 97/25002 | 7/1997 | WO | | 00/72764 | 12/2000 |
| WO | WO 97/27898 | 8/1997 | WO | | 00/74579 | 12/2000 |
| WO | WO97/31575 | 9/1997 | WO | | 00/76405 | 12/2000 |
| WO | 97/47261 | 12/1997 | WO | | 01/08601 | 2/2001 |
| WO | 98/07399 | 2/1998 | WO | | 01/12074 | 2/2001 |
| WO | 98/19608 | 5/1998 | WO | | 01/15607 | 3/2001 |
| WO | 98/19618 | 5/1998 | WO | | 01/17440 | 3/2001 |
| WO | 98/19625 | 5/1998 | WO | | 01/19257 | 3/2001 |
| WO | WO 98/19629 | 5/1998 | WO | | 01/19259 | 3/2001 |
| WO | WO 98/19630 | 5/1998 | WO | | 01/19284 | 3/2001 |
| WO | 98/19631 | 5/1998 | WO | | 01/34037 | 5/2001 |
| WO | 98/19632 | 5/1998 | * cited by examiner | | | |

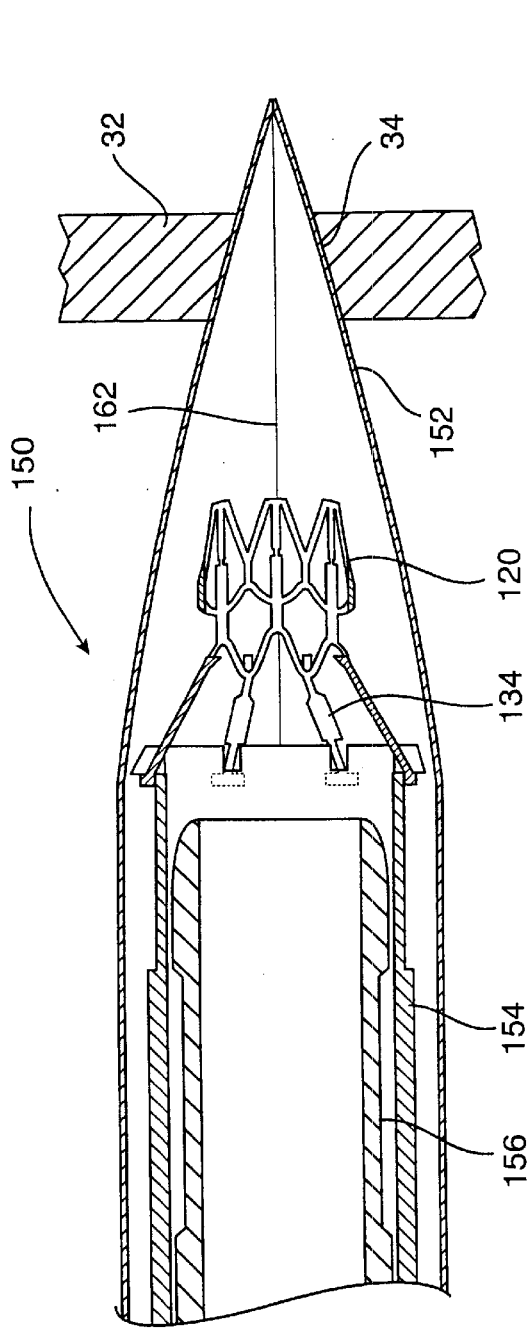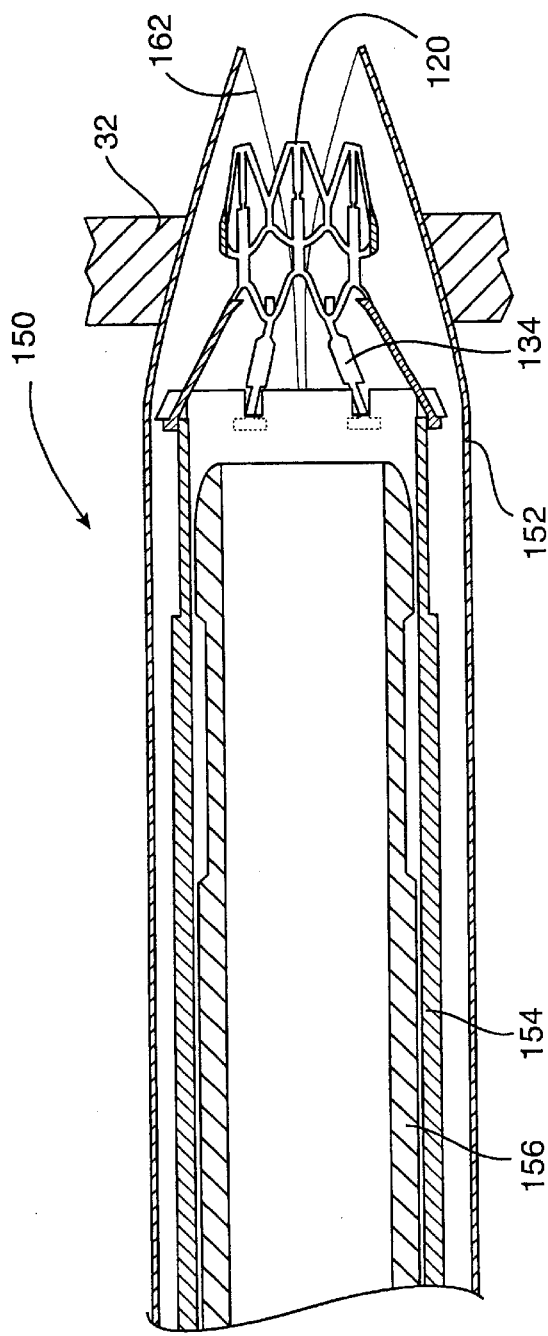

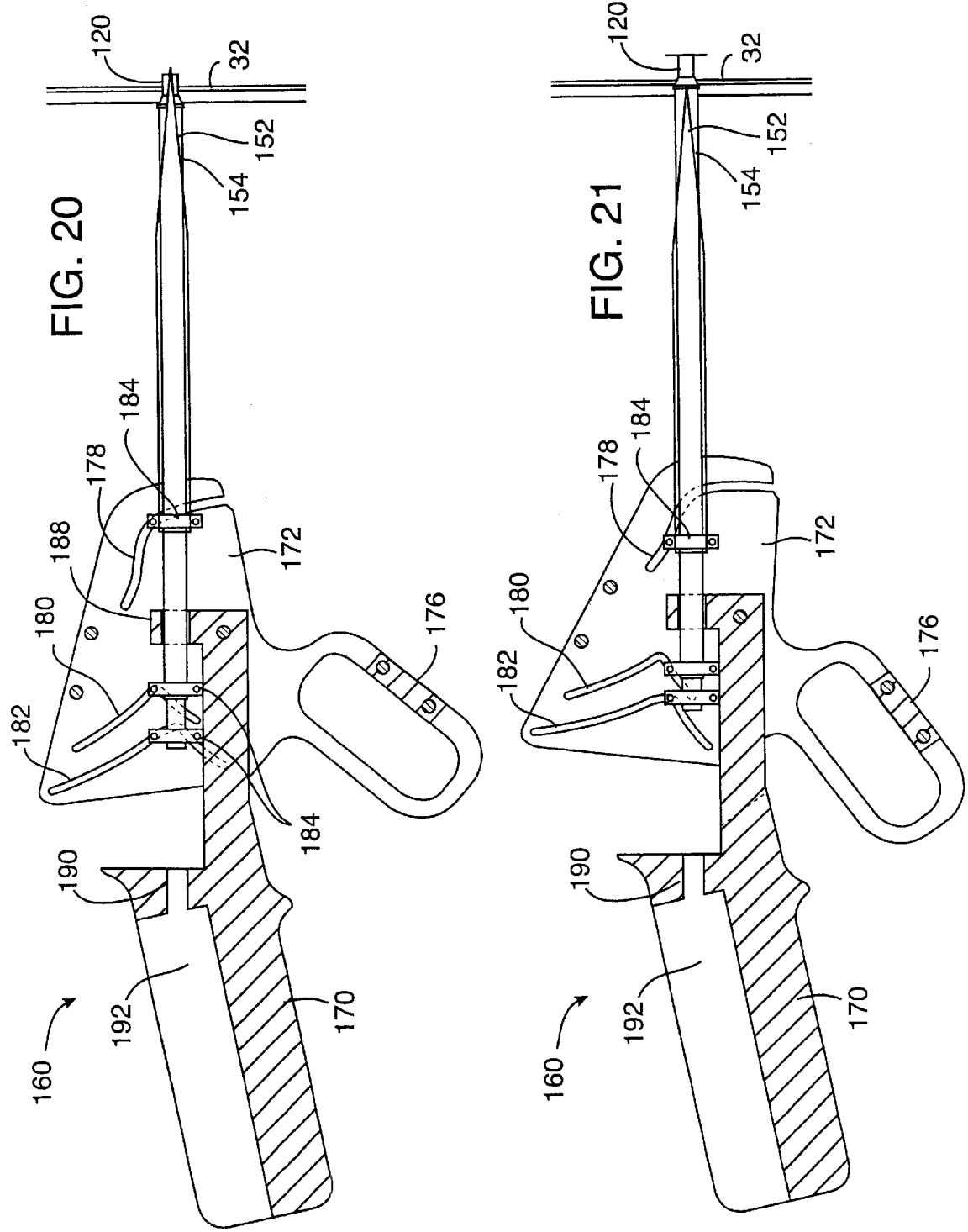

US 6,652,541 B1

METHOD OF SUTURELESS CLOSURE FOR CONNECTING BLOOD VESSELS

This application is a divisional of application Ser. No. 09/314,278, filed May 18, 1999 now U.S. Pat. No. 6,428,550, which claims priority to U.S. application Ser. No. 09/132,711, filed Aug. 12, 1998.

BACKGROUND OF THE INVENTION

1. Field of the Invention

The invention relates to an anastomosis device and method, and more particularly, the invention relates to an anastomosis device and a deployment system for forming a sutureless connection between two blood vessels.

2. Brief Description of the Related Art

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart lung machine is used to circulate the patient's blood so that the heart can be stopped and the anastomosis can be performed. In order to minimize the trauma to the patient induced by conventional CABG, less invasive techniques have been developed in which the surgery is performed through small incisions in the patients chest with the aid of visualizing scopes. Less invasive CABG can be performed on a beating or stopped heart and thus may avoid the need for cardiopulmonary bypass.

In both conventional and less invasive CABG procedures, the surgeon has to suture one end of the graft vessel to the coronary artery and the other end of the graft vessel to a blood supplying vein or artery, such as the aorta. The suturing process is a time consuming and difficult procedure requiring a high level of surgical skill. In order to perform the suturing of the graft to the coronary artery and the blood supplying artery the surgeon must have relatively unobstructed access to the anastomosis sites within the patient. In the less invasive surgical approaches, some of the major anastomosis sites cannot be easily reached by the surgeon because of their location. This makes suturing either difficult or impossible without opening up the chest cavity.

An additional problem with CABG is the formation of thrombi and atherosclerotic lesions at and around the grafted artery, which can result in the reoccurrence of ischemia. Thrombi and atherosclerotic lesions may be caused by the configuration of the sutured anastomosis site. For example, an abrupt edge at the anastomosis site may cause more calcification than a more gradual transition. However, the preferred gradual transition is difficult to achieve with conventional suturing methods.

Accordingly, it would be desirable to provide a sutureless vascular anastomosis device which easily connects a graft to a target vessel. It would also be desirable to provide a sutureless anastomosis device which is formed of one piece and is secured to the target vessel in a single step.

SUMMARY OF THE INVENTION

The present invention relates to an anastomosis device for connecting an end of a graft vessel to a target vessel. The anastomosis includes a first linkage formed of a plurality of struts and a plurality of axial members. The first linkage is expandable from a first configuration in which the first linkage is a substantially cylindrical shape to a second configuration in which the first linkage includes a first radially extending flange. A substantially cylindrical central connecting portion extends from the first linkage. A second linkage is configured to form a second radially extending flange spaced from the first radially extending flange.

In accordance with an additional aspect of the present invention, an anastomosis device for connecting an end of a graft vessel to a target vessel includes an expandable device formed from a plurality of struts and deformable from a first configuration in which the device is substantially tubular to a second configuration in which the device includes a first radial flange and a second radial flange spaced from the first radial flange a distance sufficient to accommodate a wall of a blood vessel. A first end of the expandable device includes a first linkage which changes from a substantially tubular configuration to a radially extending configuration to form the first flange upon radial expansion of the first end by an expander positioned in a center of the expandable device. A second end of the expandable device includes a second linkage which is configured to form the second radial flange upon deployment of the device.

In accordance with another aspect of the present invention, a method of performing anastomosis includes the steps of providing a one-piece tubular anastomosis device; everting an end of a graft vessel around the anastomosis device; puncturing a target vessel with a trocar; inserting the tubular anastomosis device with everted graft vessel into the puncture in the target vessel; radially expanding the tubular anastomosis device with an expander to cause portion of the tube to fold outward forming a first annular flange; and forming a second annular flange on the anastomosis device to trap a wall of the target vessel between the first and second annular flanges and seal the graft vessel to the target vessel.

In accordance with a further aspect of the present invention, an anastomosis device deployment system includes a handle, a holder tube attached to the handle, and an expander positioned within the holder and slidable with respect to the holder to a position at which the expander is positioned within the anastomosis device to radially expand the anastomosis device. The holder tube has a distal end configured to hold the anastomosis device with an attached graft vessel.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 15 is a side cross sectional view of the anastomosis device deployment system puncturing the target vessel to advance the anastomosis device into the target vessel wall;

FIG. 16 is a side cross sectional view of the anastomosis device deployment system advancing the anastomosis device into the target vessel wall;

FIG. 20 is a schematic side cross-sectional view of the deployment tool of FIG. 19 shown during an anastomosis device insertion step;

FIG. 21 is a schematic side cross-sectional view of the deployment tool of FIG. 19 shown during an anastomosis device expansion step;

DETAILED DESCRIPTION OF THE PREFERRED EMBODIMENTS

The present invention relates to an anastomosis device and method for connecting a graft vessel to a target vessel without the use of conventional sutures. The anastomosis device according to the present invention can be deployed with a deployment system which greatly increases the speed with which anastomosis can be performed over prior art suturing methods. In addition, the anastomosis device provides a smooth transition between the graft vessel and the target vessel. The devices according to the present invention are particularly designed for use in connecting graft vessels to blood delivery or target vessels. Suturing a graft vessel to a target vessel is difficult with conventional techniques, particularly in minimally invasive procedures where space may be limited. However, with an anastomosis device and deployment system of the present invention, anastomosis can be performed efficiently and effectively in tight spaces.

Figure 1:
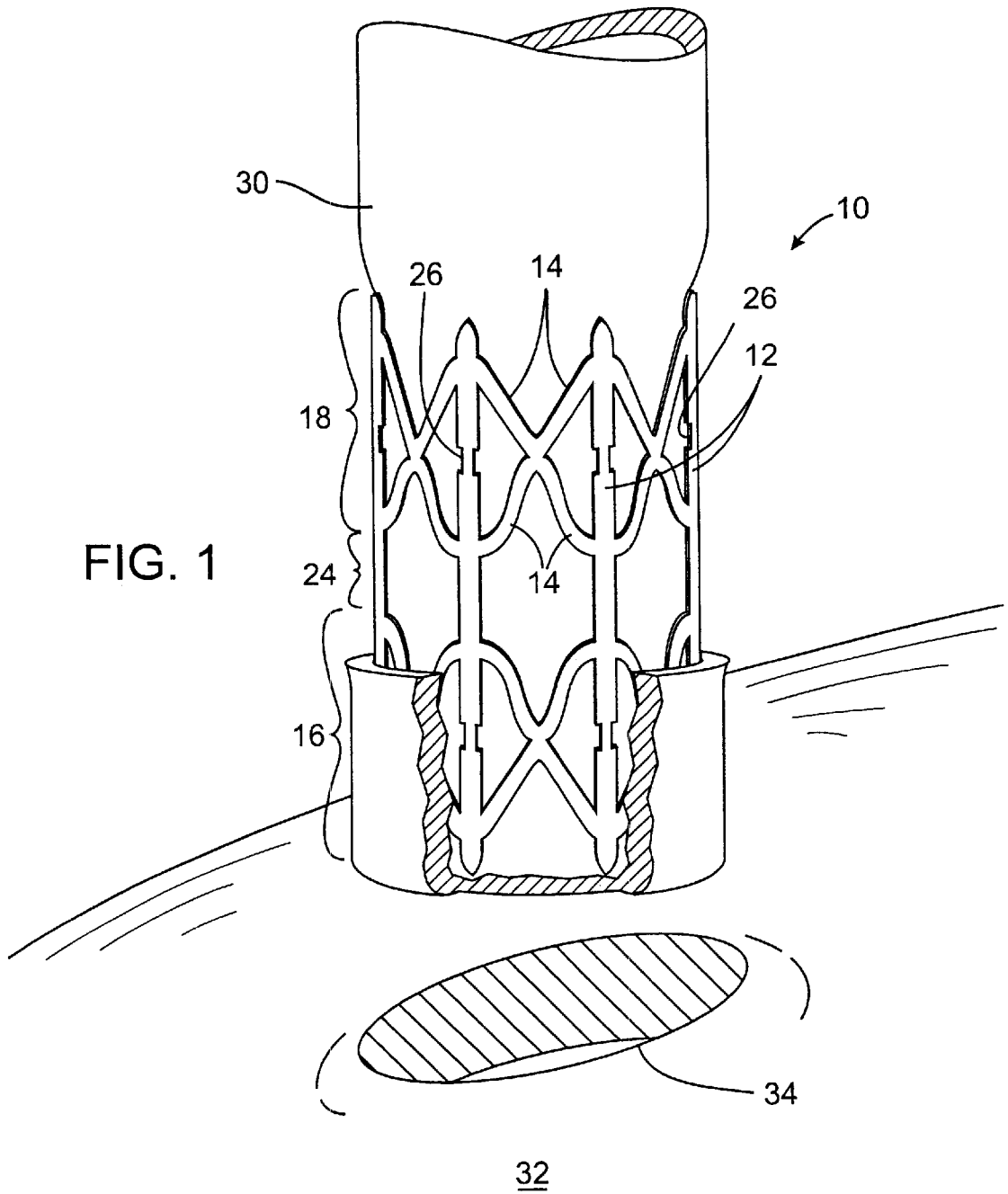
FIG. 1 is a perspective view of a first embodiment of an anastomosis device in a configuration prior to use with a graft vessel everted over the device.
Figure 2:
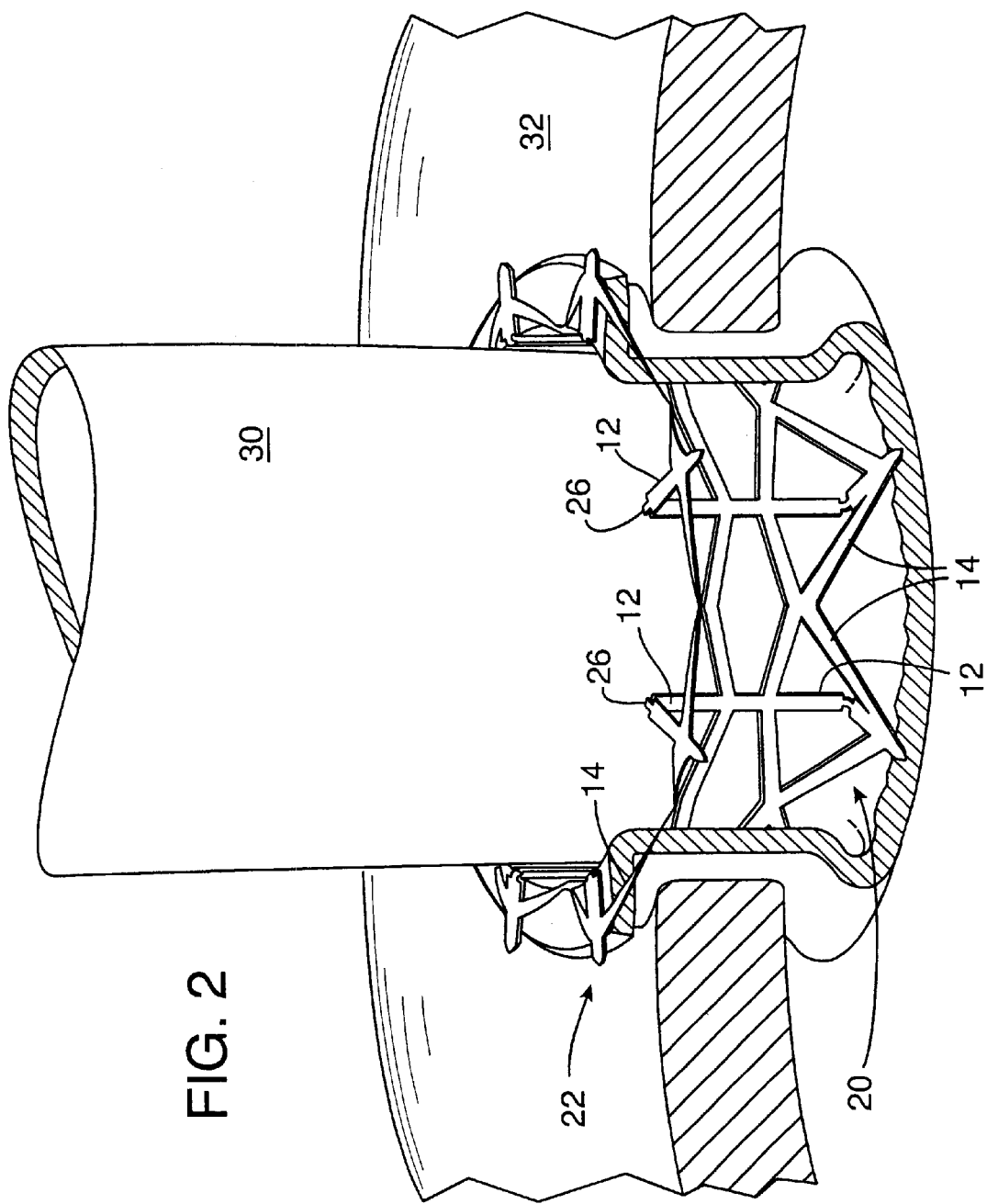
FIG. 2 is a perspective view of the anastomosis device of FIG. 1 in a deployed configuration.

FIG. 1 illustrates an anastomosis device 10 according to a first embodiment of the present invention. The anastomosis device 10 includes a plurality of axial members 12 and a plurality of struts 14 interconnecting the axial members. The axial members 12 and struts 14 form a first linkage 16 at a first end of the device and a second linkage 18 at a second end of the device. The first and second linkages 16, 18 form first and second flanges 20, 22 when the anastomosis device 10 is deployed as illustrated in FIG. 2. The deployed flanges 20, 22 may be annular ring shaped or conical in shape. The first and second linkages 16, 18 are connected by a central connecting portion 24.

In use, a graft vessel 30 is inserted through a center of the tubular anastomosis device 10 and is everted over the first linkage 16 at the first end of the device. The first end of the device may puncture part way or all the way through the graft vessel wall to hold the graft vessel 30 on the device. An opening 34 is formed in the target vessel 32 to receive the graft vessel 30 and anastomosis device 10. Once the anastomosis device 10 with everted graft vessel 30 are inserted through the opening 34 in the target vessel 32, the first and second flanges 20, 22 are formed as shown in FIG. 2 to secure the graft vessel to the target vessel by trapping the wall of the target vessel between the two flanges. The anastomosis device 10 forms a smooth transition between the target vessel 32 and the graft vessel 30 which helps to prevent thrombi formation.

The first and second flanges 20, 22 are formed by radial expansion of the anastomosis device 10 as follows. The first and second linkages 16, 18 are each made up of a plurality of axial members 12 and struts 14. The struts 14 are arranged in a plurality of diamond shapes with adjacent diamond shapes connected to each other to form a continuous ring of diamond shapes around the device. One axial member 12 extends through a center of each of the diamond shapes formed by the struts 14. A reduced thickness section 26 or hinge in each of the axial members 12 provides a location for concentration of bending of the axial members. When an expansion member such as a tapered rod or an inflatable balloon is inserted into the tubular anastomosis device 10 and used to radially expand the device, each of the diamond shaped linkages of struts 14 are elongated in a circumferential direction causing a top and bottom of each of the diamond shapes to move closer together. As the top and bottom of the diamond shapes move closer together, the axial members 12 bend along the reduced thickness sections 26 folding the ends of the device outward to form the first and second flanges 20, 22. Once the first and second flanges 20, 22 have been formed, the wall of the target vessel 32 is trapped between the flanges and the everted graft vessel 30 is secured to the target vessel.

In the anastomosis device 10 shown in FIGS. 1 and 2, the struts 14 may be straight or curved members having constant or varying thicknesses. In addition, the axial members 12 may have the reduced thickness sections 26 positioned at a center of each of the diamond shapes or off center inside the diamond shapes. The positioning and size of the reduced thickness sections 26 will determine the location of the flanges 20, 22 and an angle the flanges make with an axis of the device when fully deployed. A final angle between the flanges 20, 22 and longitudinal axis of the device 10 is about 40–100 degrees, preferably about 50–90 degrees.

Figure 3:
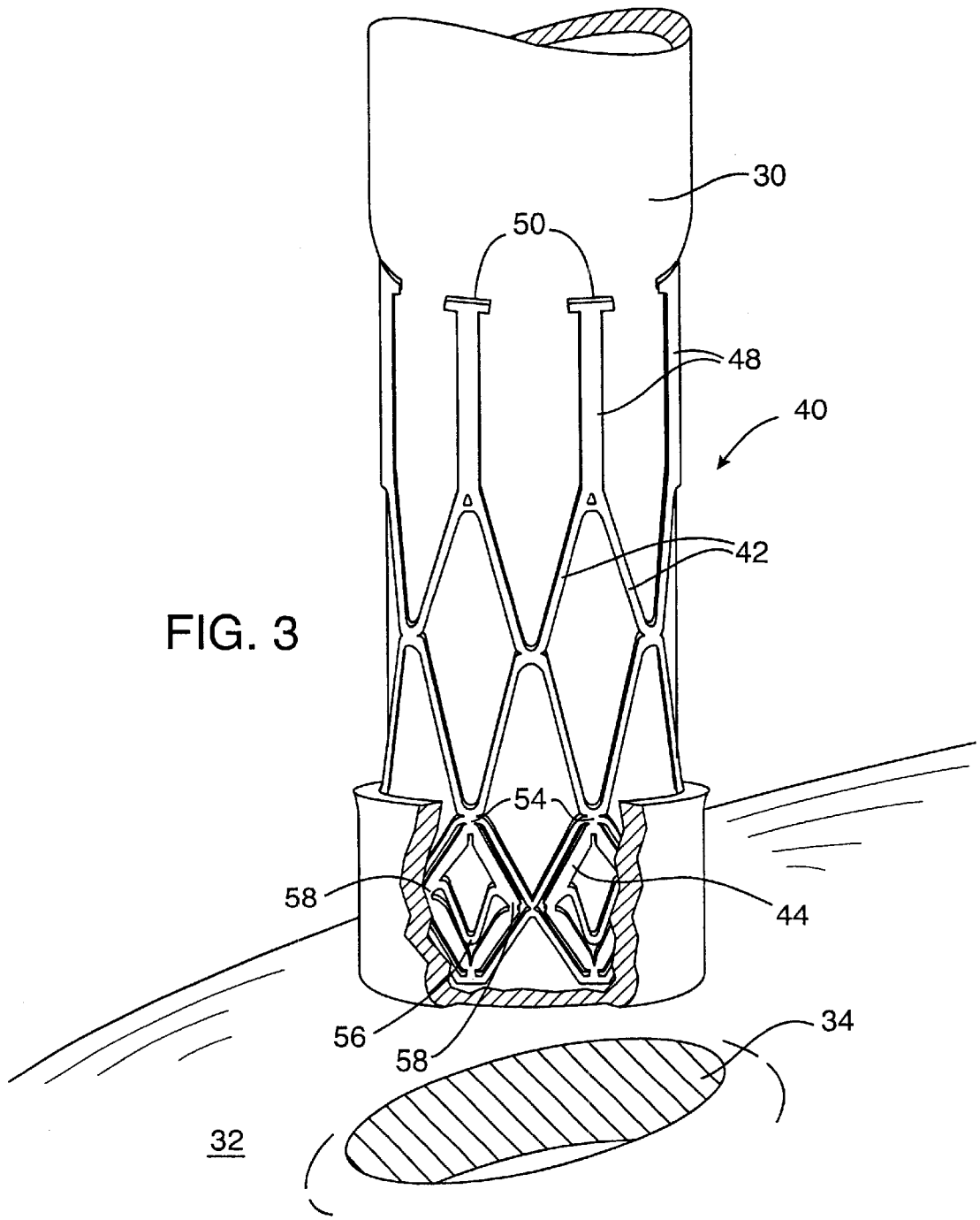
FIG. 3 is a perspective view of a second embodiment of an anastomosis device in a configuration prior to use with a graft vessel everted over the device.
Figure 4:
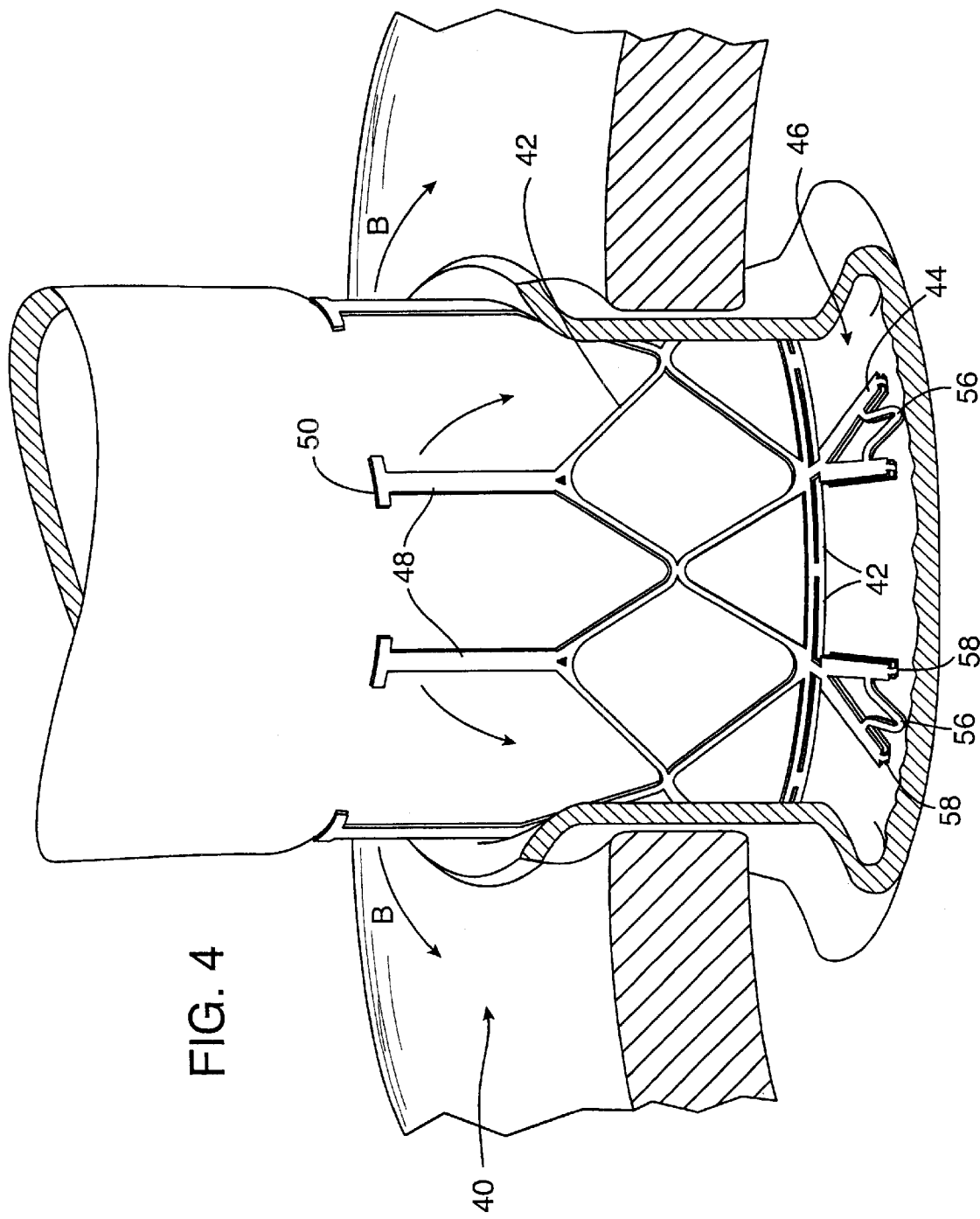
FIG. 4 is a perspective view of the anastomosis device of FIG. 3 in a deployed configuration.

FIG. 3 illustrates a second embodiment of a tubular anastomosis device 40 formed of a plurality of struts 42 interconnected in a diamond pattern. A first end of the device includes a plurality of interior diamonds 44 positioned within the diamonds formed by the plurality of struts 42. When the device is deployed, as illustrated in FIG. 4, the interior diamonds 44 fold outward to form a first annular flange 46. A second end of the device 40 includes a plurality of pull tabs 48 each having a T-shaped end 50 to be received in a corresponding slot in a deployment device. The deployment device holds the anastomosis device 40 during positioning and deployment of the first flange 46. Once the first annular flange 46 has been formed, the pull tabs 48 are folded radially outward and downward in the direction of the arrows B to form a second annular flange (not shown). Although the pull tabs 48 have been illustrated with T-shaped ends, the pull tabs may have other configurations such as loops which engage hooks of a deployment device.

In use, the graft vessel 30 is inserted through a center of the tubular anastomosis device 40 and everted over the first end of the device as shown in FIG. 3. An opening 34 is formed in the target vessel 32 and the anastomosis device 40 with the everted graft vessel 30 are inserted through the opening 34 in the target vessel. An expander is then advanced axially through the anastomosis device 40 to radially expand the device and cause the deployment of the first annular flange 46. During advancement of the expander, the device 40 is held in place by the deployment device which is connected to the T-shaped ends 50 of the pull tabs 48. After deployment of the first annular flange 46 the expander is removed and the pull tabs 48 are disconnected from the deployment device and folded outward in the direction of the arrows B in FIG. 4 to form the second annular flange. The wall of the target vessel 32 is trapped between the first and second annular flanges.

In the embodiment of FIGS. 3 and 4, the interior diamonds 44 which form the first annular flange 46 each include top and bottom reduced thickness connection members 54 which connect the interior diamonds 44 to the struts 42. Each of the interior diamonds 44 also include a U-shaped web member 56 and two reduced thickness portions 58 located at opposite sides of the interior diamonds. As the device 40 is radially expanded, the diamond shapes formed by the struts 42 become more elongated in a circumferential direction, shortening the height of each of these diamond shapes. As the height of the diamond shapes formed by the struts 42 decreases, the interior diamonds 44 are folded outward into the configuration illustrated in FIG. 4. When the device 40 is fully expanded and the first annular flange 46 is fully formed, the diamonds which originally surrounded the interior diamonds 44 are completely extended and the struts 42 which originally formed the diamonds are parallel or substantially parallel. The interior diamonds 44 are each folded in half at the reduced thickness portions 58 or hinges.

Figure 5:
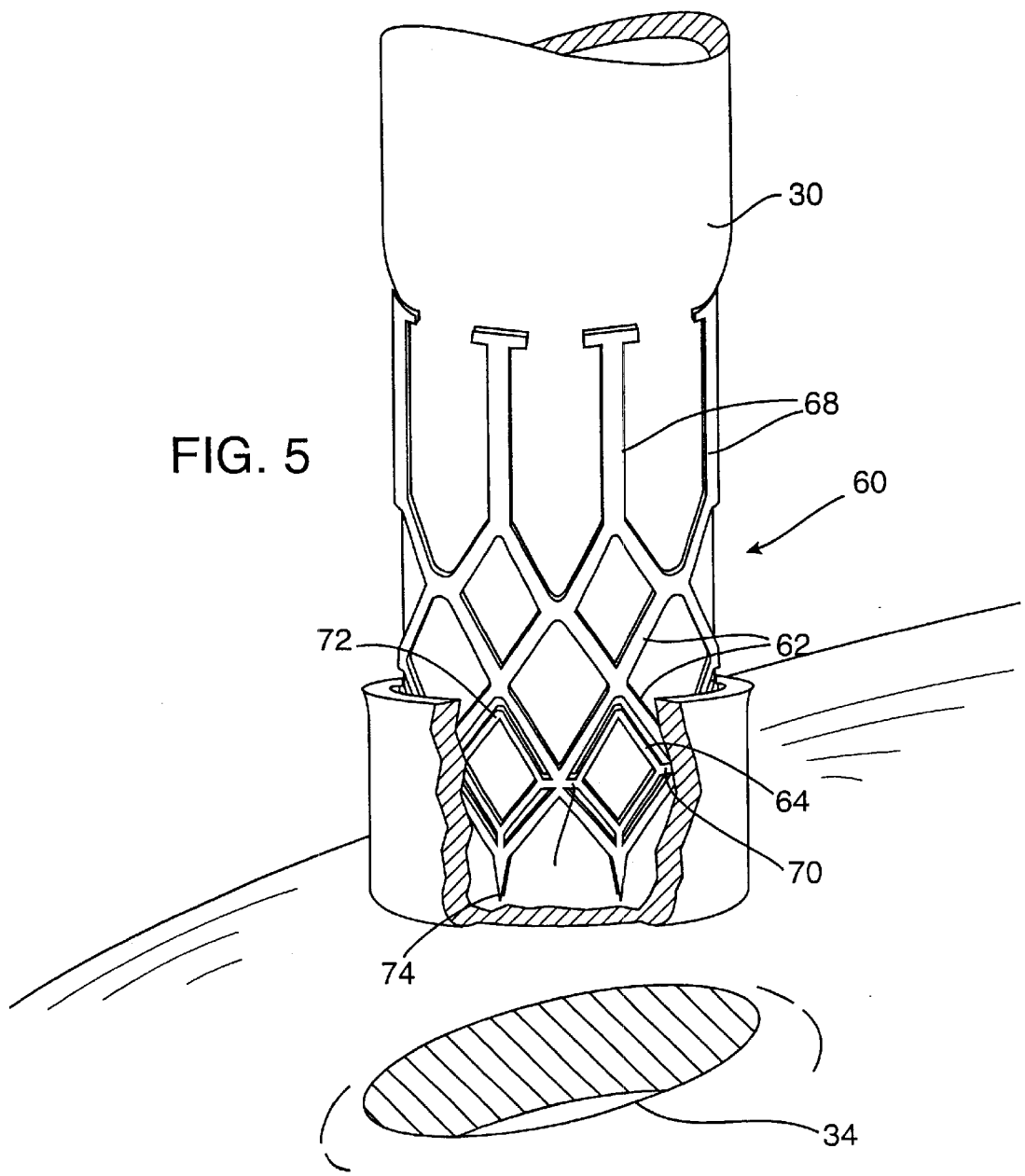
FIG. 5 is a perspective view of a third embodiment of an anastomosis device in a configuration prior to use with a graft vessel everted over the device.
Figure 6:
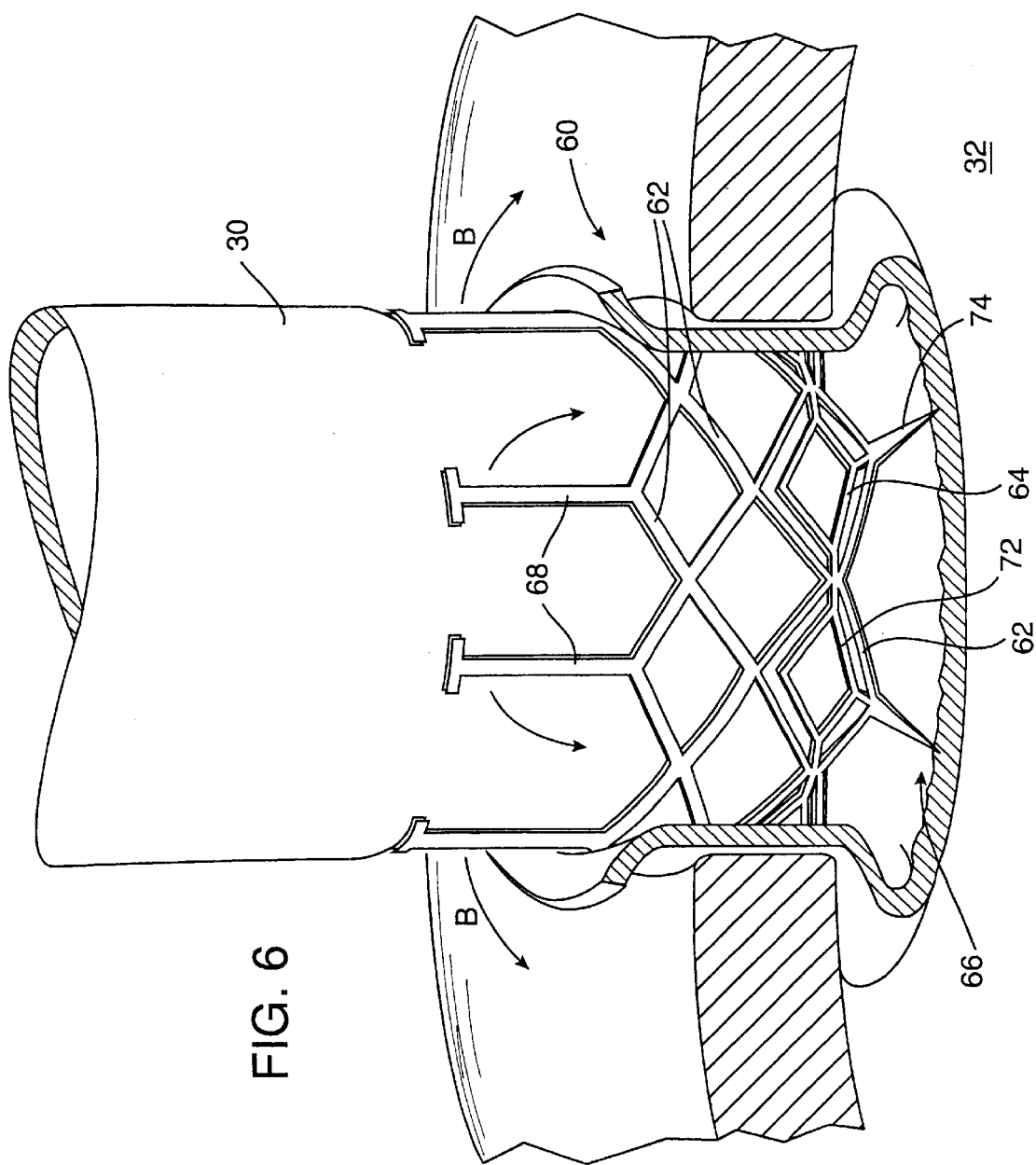
FIG. 6 is a perspective view of the anastomosis device of FIG. 5 in a deployed configuration.

FIGS. 5 and 6 illustrate a third embodiment of a tubular anastomosis device 60 having a plurality of struts 62, interior diamonds 64, and a plurality of pull tabs 68. The anastomosis device 60 of FIGS. 5 and 6 differs from the anastomosis device 40 of FIGS. 3 and 4 in the arrangement of the interior diamonds 64. The interior diamonds 64, as illustrated in FIG. 5, are connected to the surrounding struts 62 by three connection members 70. The connection members 70 are located at opposite sides of each of the interior diamonds 64 and at the bottom of the interior diamonds. A top-corner 72 of each of the interior diamonds 64 is not connected to the struts and folds inward upon expansion of the device.

With this embodiment of FIGS. 5 and 6, as an expander is inserted axially through the anastomosis device 60, the top corners 72 of each of the interior diamonds 64 fold inwardly while a bottom edge of the device folds outwardly to form the first annular flange 66. The expander may also push on the inwardly folded top corners 72 of the interior diamonds 64 to further bend the first flange 66 outward. The device 60 also includes a plurality of pointed ends 74 which puncture the everted graft vessel 30 and help to retain the graft vessel on the anastomosis device 60.

In use, the anastomosis device 60 is provided with a graft vessel 30 which is inserted through a center of the device and everted over the pointed ends 74 and interior diamonds 64 of the device. The anastomosis device 60 and everted graft vessel 30 are then inserted in the opening 34 in the target vessel 32 and the first annular flange 66 is deployed by expansion of the device with an axially movable expander. After formation of the first annular flange 66, the pull tabs 68 are folded downward and outward in the direction of the arrows B illustrated in FIG. 6 to form the second annular flange and trap the wall of the target vessel between the first and second annular flanges.

Figure 7:
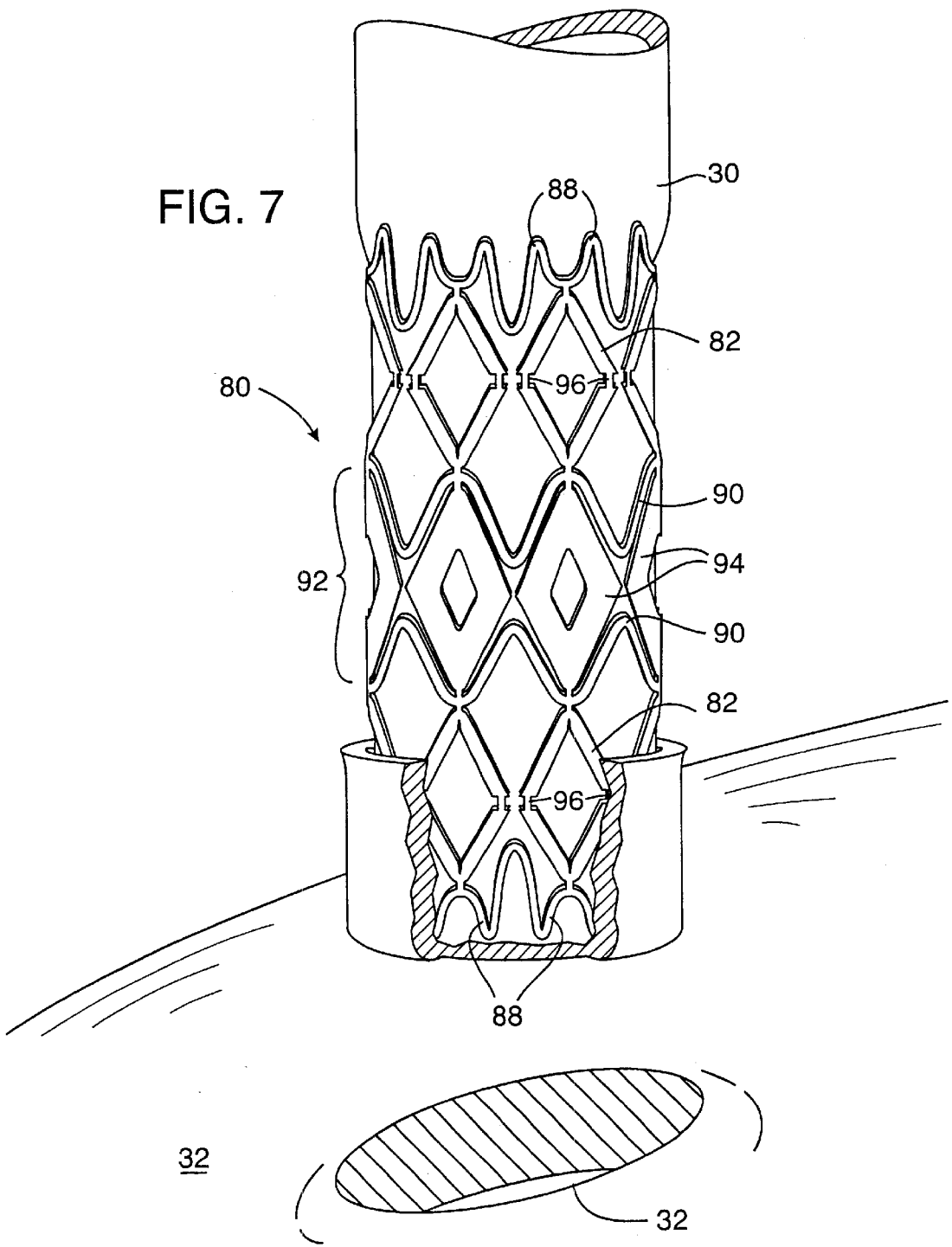
FIG. 7 is a perspective view of a fourth embodiment of an anastomosis device in a configuration prior to use with a graft vessel everted over the device.
Figure 8:
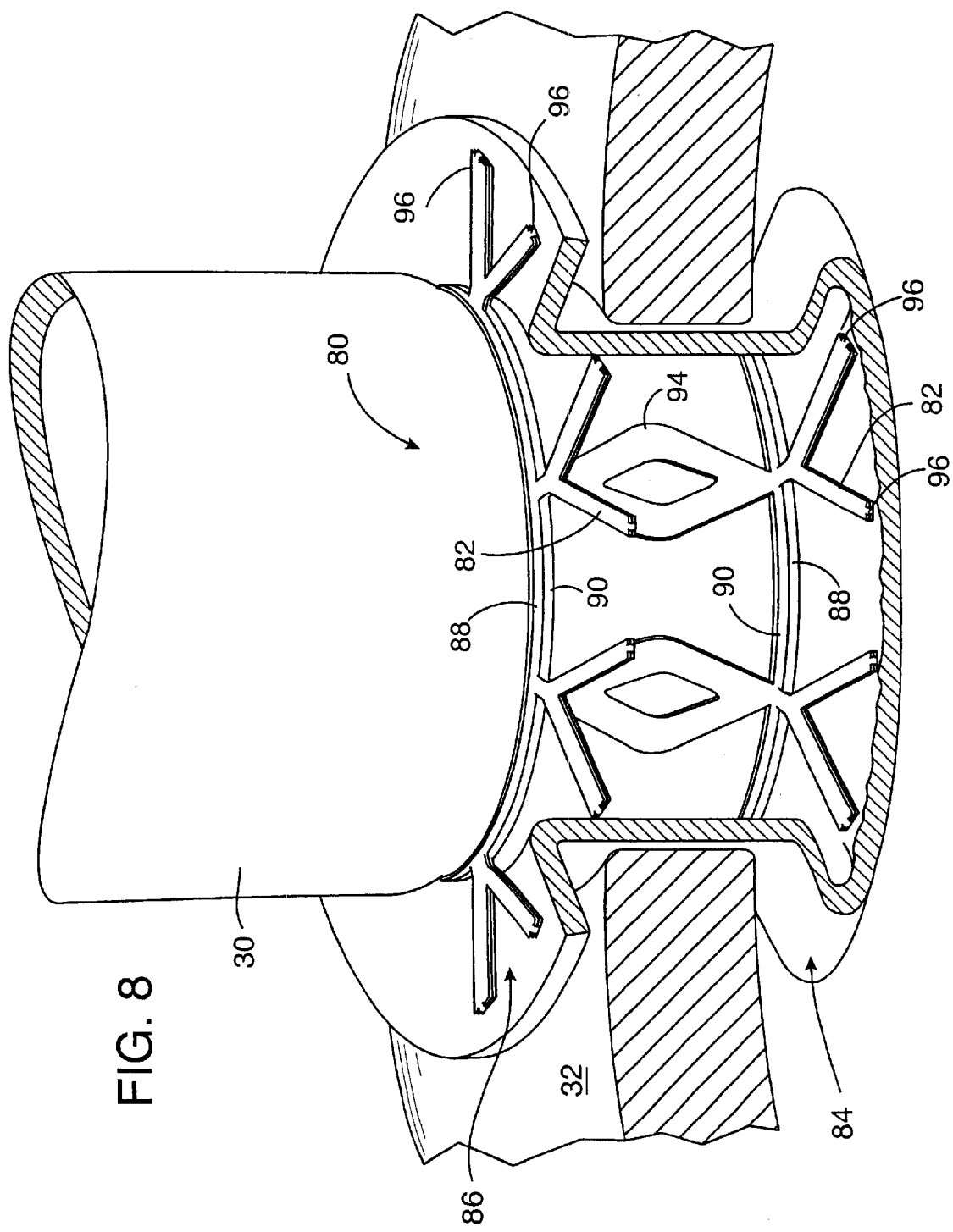
FIG. 8 is a perspective view of the anastomosis device of FIG. 7 in a deployed configuration.

An alternative embodiment of an anastomosis device 80 illustrated in FIGS. 7 and 8 includes two rows of diamond-shaped members 82 which fold outward to form the first and second annular flanges 84, 86. Each of the diamond-shaped members 82 is connected to M-shaped struts 88 at one end and to V-shaped struts 90 at an opposite end. The diamond-shaped members 82 are connected only at the top end and bottom end. A central connecting portion 92 of the device 80 includes a plurality of large diamond-shaped support members 94. As an expander is inserted into the device 80, the device expands from a configuration illustrated in FIG. 7 to the configuration illustrated in FIG. 8 in which the first and second annular flanges 84, 86 have been formed. During expansion, the M-shaped struts 88 and the V-shaped struts 90 are extended to straight or substantially straight members and the large diamond support members 94 move away from one another. The diamond-shaped members 82 each fold in half at reduced thickness portions 96 as in the embodiment illustrated in FIGS. 3 and 4.

Figure 9:
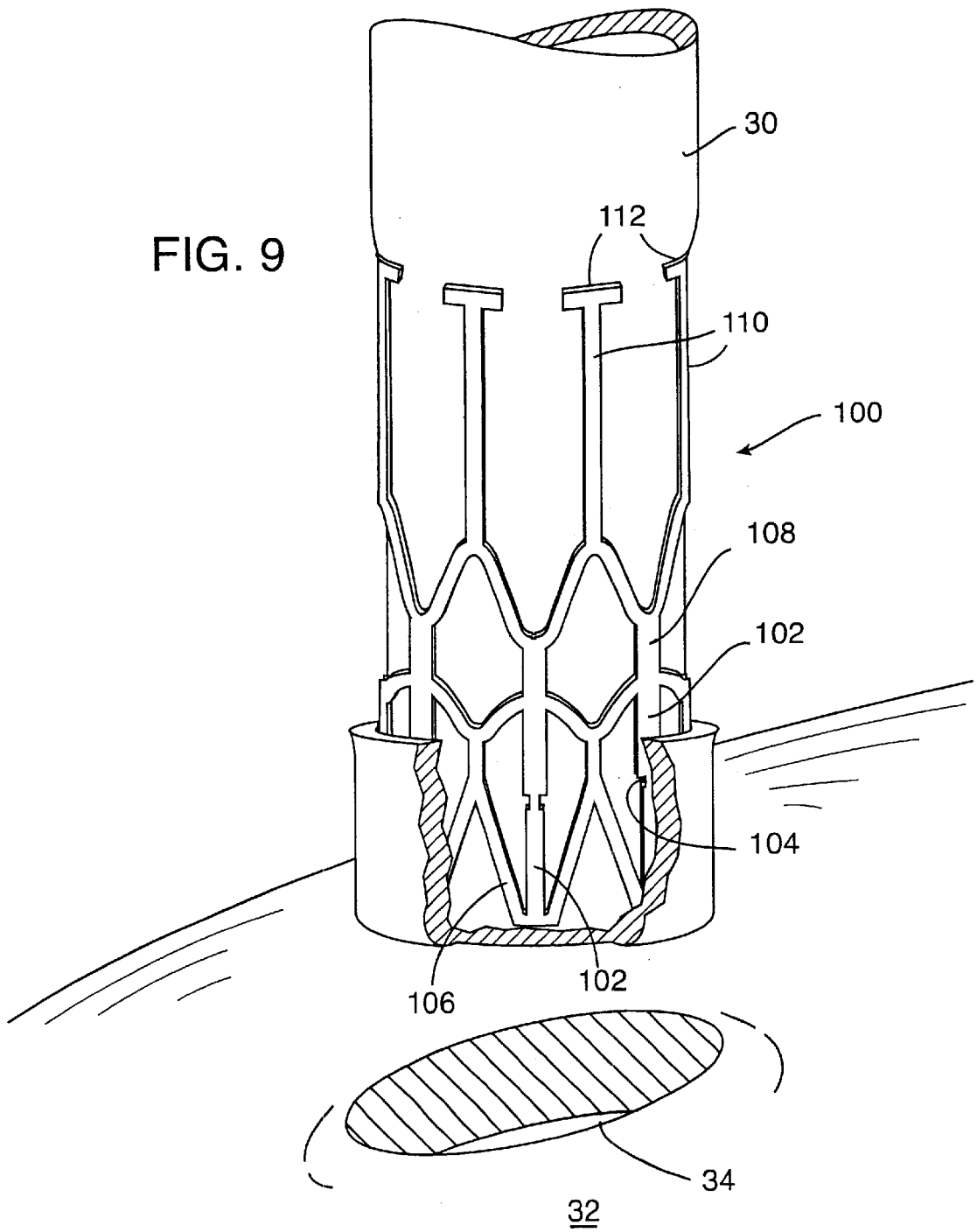
FIG. 9 is a perspective view of a fifth embodiment of an anastomosis device in a configuration prior to use with a graft vessel everted over the device.
Figure 10:
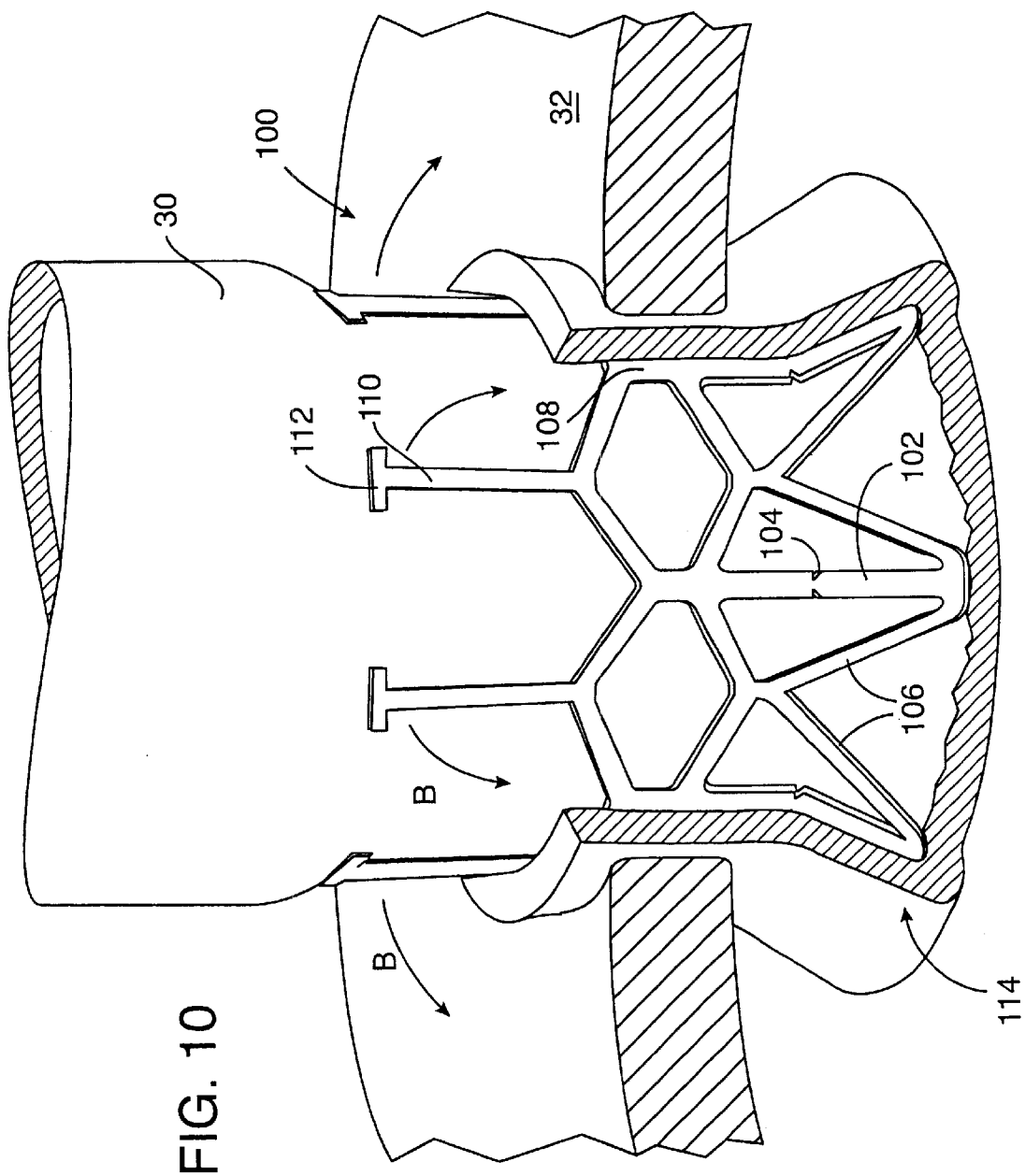
FIG. 10 is a perspective view of the anastomosis device of FIG. 9 with a bottom flange in a deployed configuration.
Figure 11:
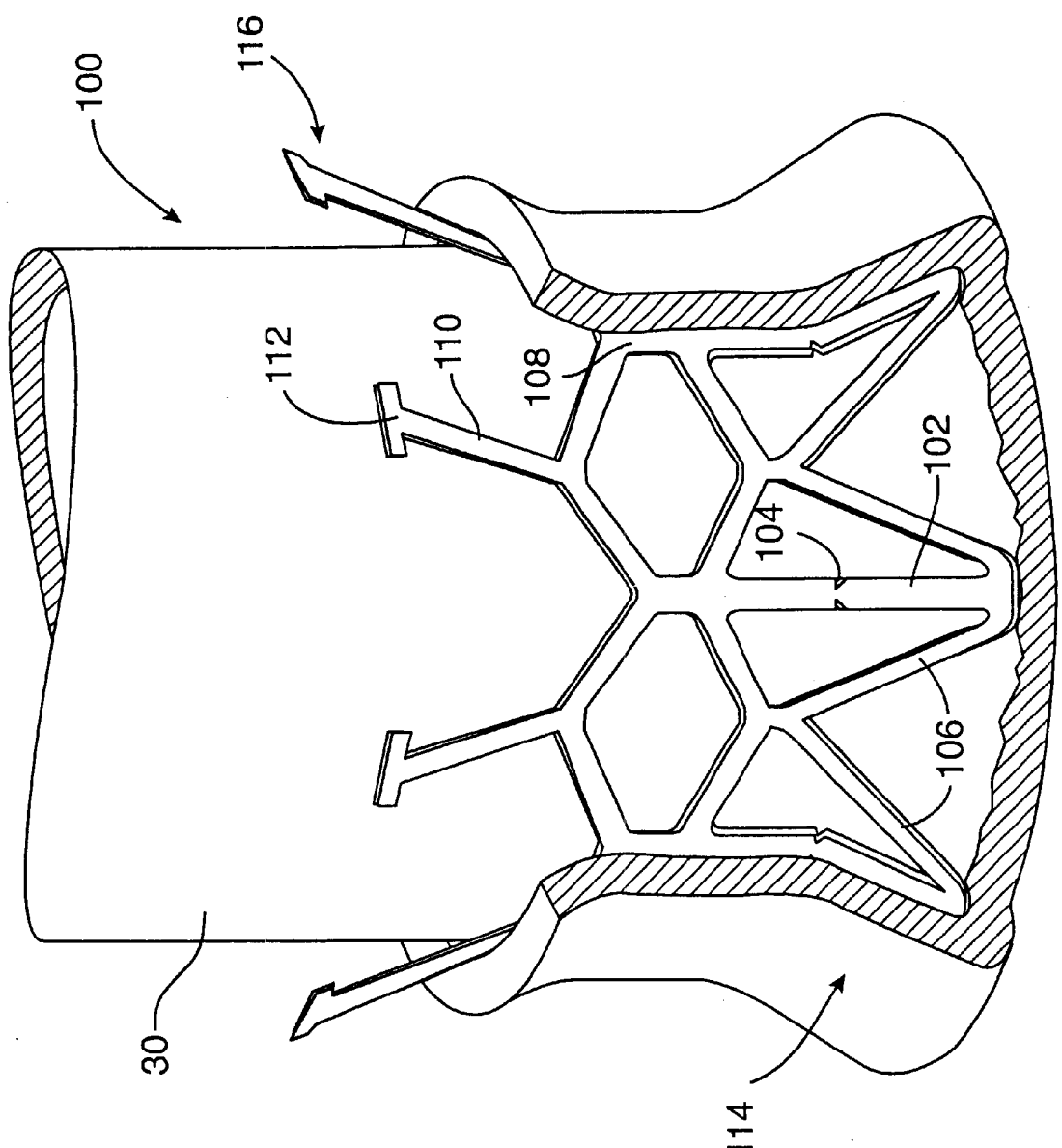
FIG. 11 is a perspective view of the anastomosis device of FIG. 9 with a bottom flange and a top flange both in deployed configurations.

FIGS. 9–11 illustrate a further alternative embodiment of an anastomosis device 100 according to the present invention. The device 100 includes a plurality of axial members 102 having reduced thickness portions 104. Each of the axial members 102 is positioned within a multi-sided expandable linkage 106. A central connecting portion 108 connects the expandable linkage 106 to a plurality of pull tabs 110. Each of the pull tabs 110 has a T-shaped end 112 which is received in a corresponding slot in a deployment device to hold the anastomosis device 100 during insertion and expansion. However, other pull tab shapes may also be used. As an expander is inserted axially into the anastomosis device 100, the linkage 106 expands causing the axial members 102 to fold along the reduced thickness portions 104 and extend radially outward forming a first radial flange 114, as illustrated in FIG. 10. The first radial flange 114 may be configured to extend at an acute angle from an axis of anastomosis device 100 or may be folded to form an angle of up to 90 degrees or greater. The angle between the axis of anastomosis device and the lower portion of the axial members 102 after the first radial flange 114 has been deployed is preferably between about 40 and 100 degrees. After the first radial flange has been deployed, the pull tabs 110 are disengaged from the deployment device and folded outwards in the direction of the arrows B to form a second radial flange 116 as illustrated in FIG. 11. To disengage and fold the pull tabs 110 outwards, the deployment device is moved distally with respect to the anastomosis device. The first and second radial flanges 114, 116 trap a wall of the target vessel 32 between the flanges and thus secure the everted graft vessel 30 to the target vessel.

Figure 12:
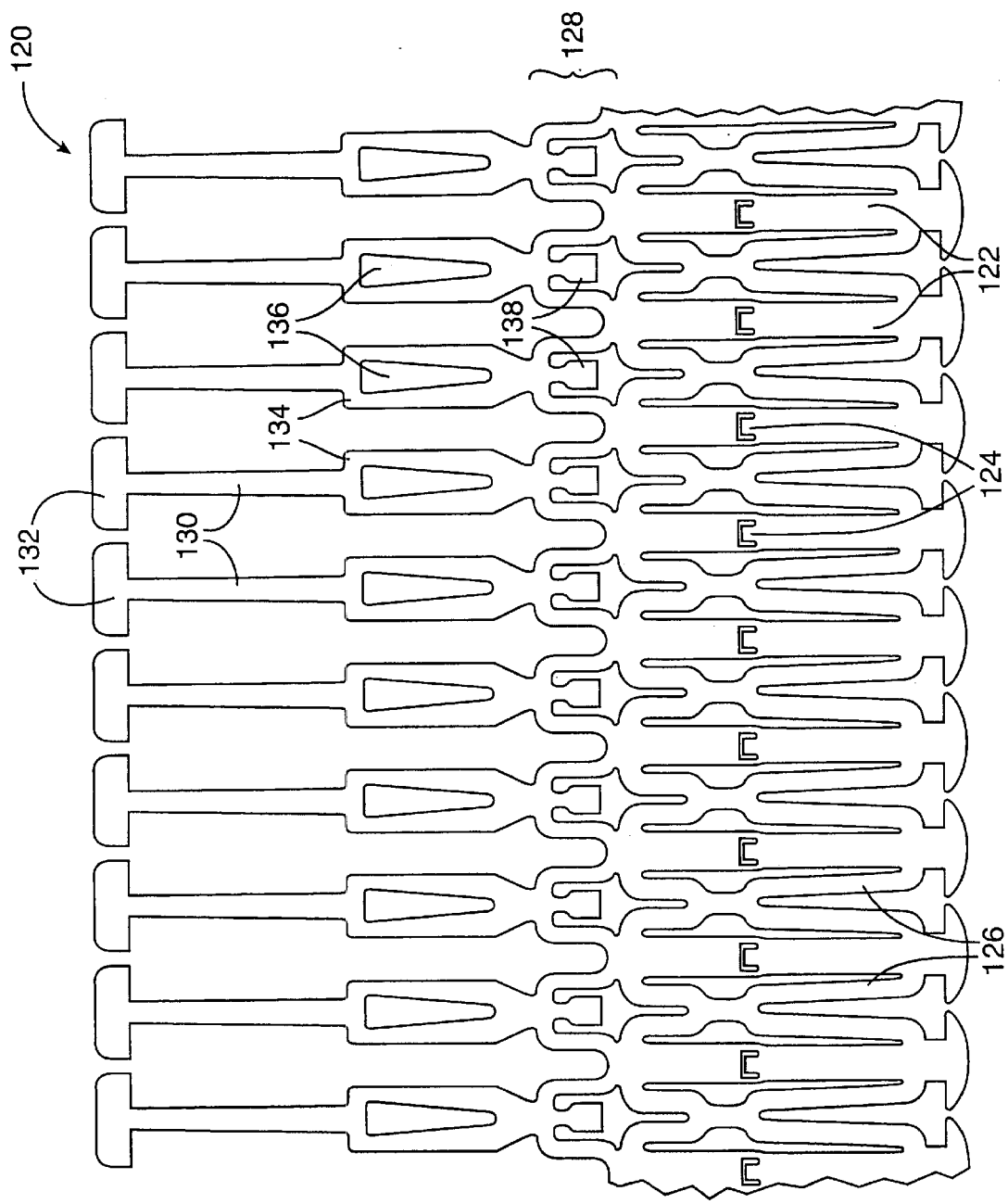
FIG. 12 is a side view of a portion of a sixth embodiment of an anastomosis device which has been laid flat for ease of illustration.
Figure 13:
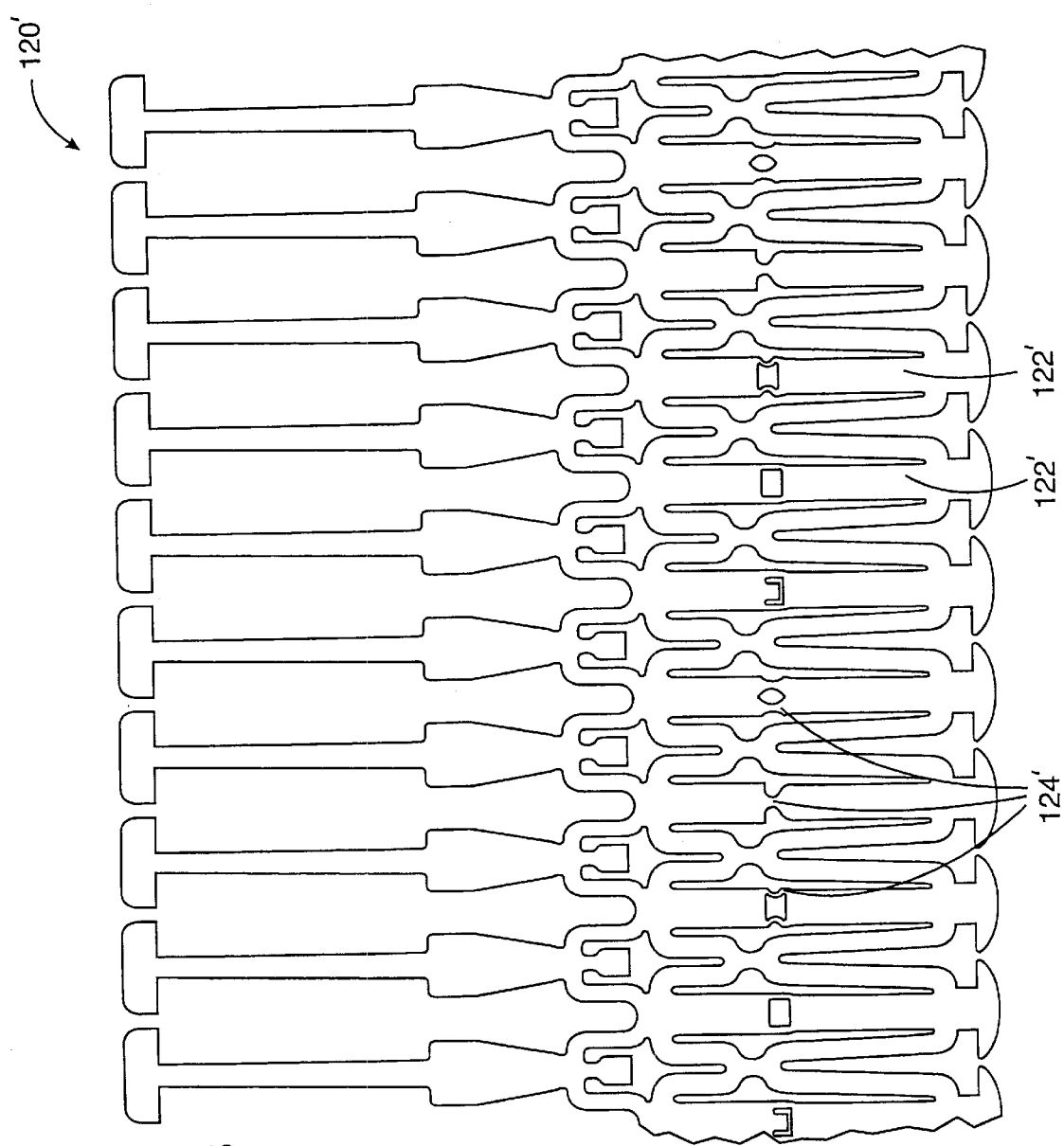
FIG. 13 is a side view of a portion of a seventh embodiment of an anastomosis device which has been laid flat for ease of illustration.

FIGS. 12 and 13 illustrate alternative embodiments of the device 100 of FIGS. 9 through 11. The expandable tubular anastomosis device 120 of FIG. 12 has been cut and laid flat for ease of illustration. The device 120 includes a plurality of axial members 122 having hinges 124 in the form of U-shaped grooves. The axial members 122 are each mounted at opposite ends in an expandable linkage 126. The expandable linkage 126 is at one end of the device 120 while an opposite end of the device includes a plurality pull tabs 130. The pull tabs 130 and linkage 126 are connected by a central connecting portion 128. Each of the pull tabs 130 has a T-shaped end 132, a shoulder 134, and a triangular slot 136. Extending from an end of each of the pull tabs 130 opposite the T-shaped ends 132 is a tab lock 138.

In use, the anastomosis device 120 of FIG. 12 is used in a manner substantially similar to that of the device shown in FIGS. 9–11. In particular, the device 120 is attached to an deployment tool by the T-shaped ends 132 of the pull tabs 130. A graft vessel is extended through the center of the tubular device 120 and everted around the end of the device opposite the pull tabs 130. An expander is advanced axially into the device to expand the expandable linkage 126 and cause the lower portion of each of the axial members 122 below the hinges 124 to bend outward to form a first flange. The material in the center of each of the U-shaped cuts which form the hinges 124 serves as a backstop to prevent the flange from bending or rolling due to radial compressive forces applied to the flange by the stretched graft vessel. In contrast, with the narrowed section hinge shown in FIG. 1 the bend at the hinge tends to roll away from the desired hinge point due to compressive forces applied by the graft vessel. The backstop hinge 124 prevents rolling of the bend along the axial member 122.

After formation of the first flange with the expander, the expander is withdrawn. During this withdrawal of the expander, an annular groove on an exterior surface of the expander engages the tab locks 138 causing the pull tabs 130 to bend outwardly to form the second flange. Alternatively, the tab locks 138 may be caught on a leading edge of the expander. As the pull tabs 130 bend outwardly, the T-shaped ends 132 of the pull tabs disengage from the deployment device. According to one embodiment of the invention, the second flange is formed by a first bend in the pull tabs 130 at a location between the triangular slot 136 and the lock tab 138 and a second bend in the pull tab at the shoulder 134. These two bends in the pull tabs 130 allow the anastomosis device to accommodate target vessels with different wall thicknesses. Each of the two bends preferably forms an angle of about 20–70 degrees.

FIG. 13 illustrates a further embodiment of a tubular anastomosis device 120' which corresponds substantially to the device shown in FIG. 12. However, FIG. 13 illustrates several different variations of hinges 124' for the axial members 122'. In particular, the hinges 124' may be formed in any of the different manners illustrated in FIG. 13 by removing material from the axial members 122' to cause bending at the desired location. These hinges 124' may include openings of various shapes and/or cut away portions on the sides of the axial members 122'. The different hinge configurations have been shown in one device only for purposes of illustration.

Figure 14:
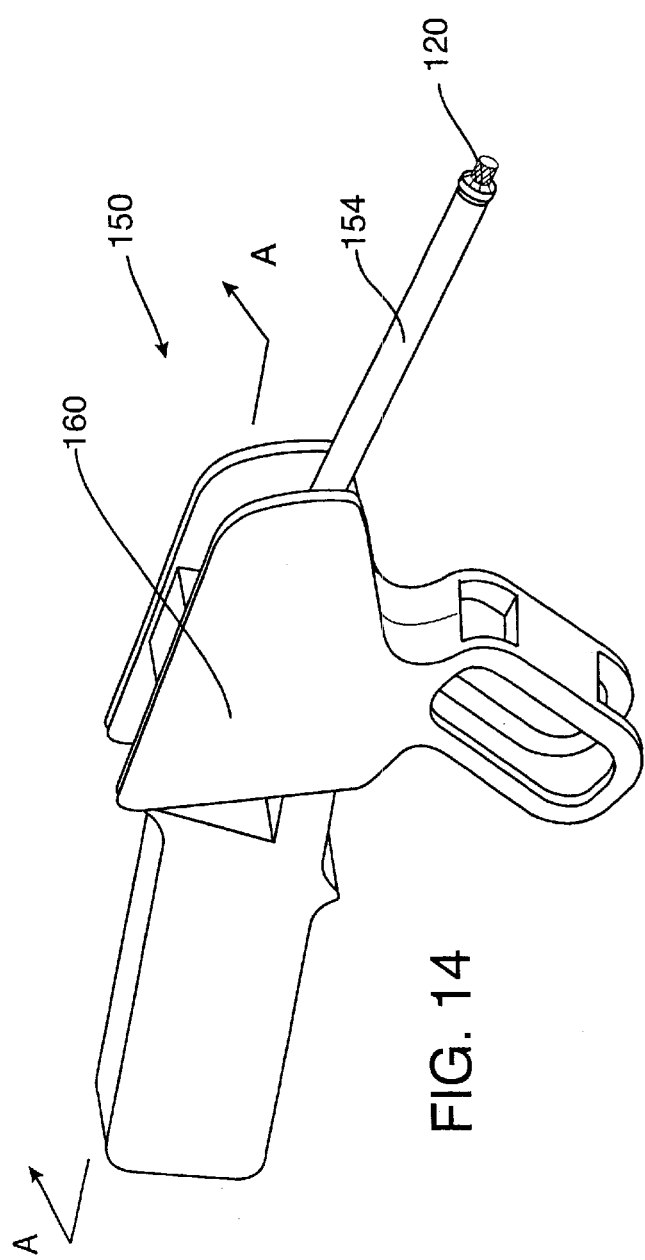
FIG. 14 is a perspective view of an anastomosis device deployment system.
Figure 14A:
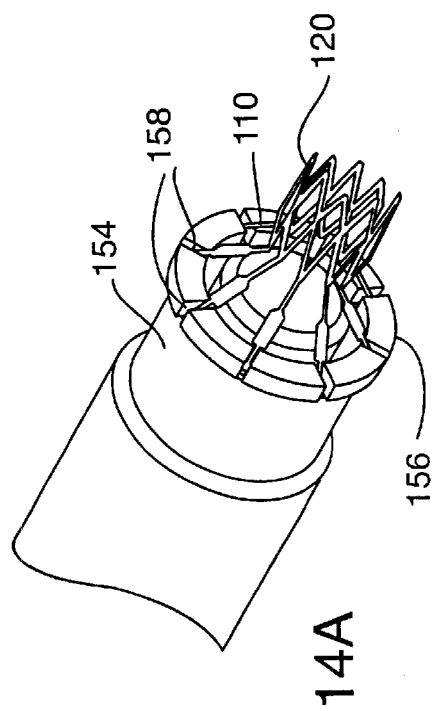
FIG. 14A is an enlarged perspective view of the distal end of the anastomosis device deployment system of FIG. 14 with an anastomosis device prior to deployment.
Figure 17:
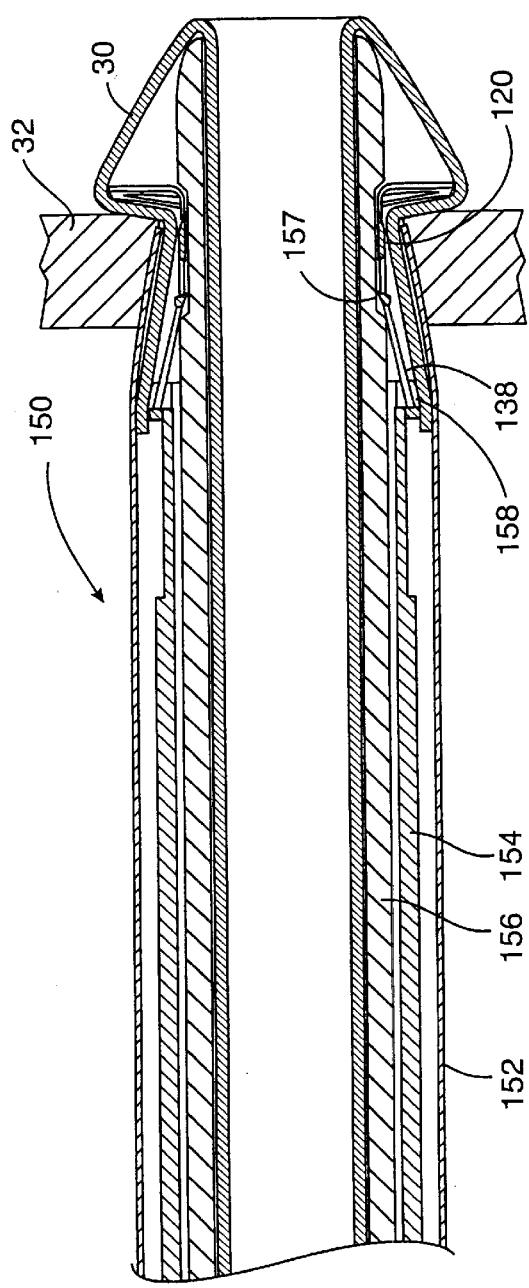
FIG. 17 is a side cross sectional view of the anastomosis device deployment system with an expanded first annular flange.

FIGS. 14–18 illustrate a deployment system 150 and sequence of deploying an anastomosis device 120 such as the device shown in FIG. 12 with the deployment system. In FIGS. 14–16 the graft vessel 30 has been eliminated for purposes of clarity. As shown in FIGS. 14–18, the deployment system 150 includes a hollow outer trocar 152 (not shown in FIG. 14), a holder tube 154 positioned inside the trocar, and an expander tube 156 slidable inside the holder tube. As can be seen in the detail of FIG. 14A, the anastomosis device 120 is attached to a distal end of the holder tube 154 by inserting the T-shaped ends 112 of each of the pull tabs 110 in slots 158 around the circumference of the holder tube. The trocar 152, holder tube 154, and expander tube 156 are all slidable with respect to one another during operation of the device. A device handle 160 is provided for moving the tubes with respect to one another will be described in further detail below with respect to FIGS. 19–22.

As shown in FIG. 15, initially, the holder tube 154, expander tube 156, and the anastomosis device 120 are positioned within the trocar 152 for insertion. The trocar 152 has a hollow generally conical tip with a plurality of axial slots 162 which allow the conical tip to be spread apart so that the anastomosis device 120 can slide through the opened trocar. The trocar 152, acting as a tissue retractor and guide, is inserted through the wall of the target vessel 32 forming an opening 34. As shown in FIG. 16, the anastomosis device 120 is then advanced into or through the target vessel wall 32 with the holder tube 154. The advancing of the holder tube 154 causes the distal end of the trocar 152 to be forced to spread apart. Once the anastomosis device 120 is in position and the trocar 152 has been withdrawn, the first annular flange is deployed by advancing the expander tube 156 into the anastomosis device. The advancing of the expander tube 156 increases the diameter of the anastomosis device 120 causing the first flange to fold outward from the device. This expanding of the first flange may be performed inside the vessel and then the device 120 may be drawn back until the flange abuts an interior of the target vessel wall 32.

Figure 18:
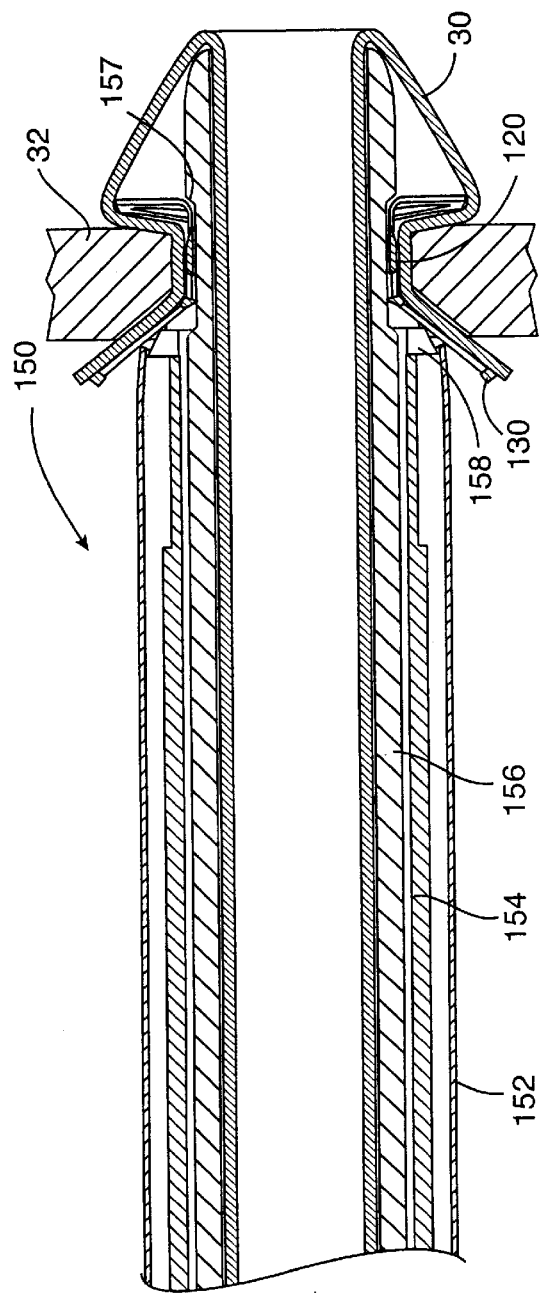
FIG. 18 is a side cross sectional view of the anastomosis device deployment system expanding a second annular flange.

As shown in FIG. 18, after the first flange has been deployed, the expander tube 156 is withdrawn forming the second flange. As the expander tube 156 is withdrawn, the anastomosis device 120 drops into a radial groove 157 on an exterior of the expander tube due to the elasticity of the device. The radial groove 157 holds the anastomosis device 120 stationary on the expander tube. The holder tube 154 is then moved forward disengaging the anastomosis device pull tabs 130 from the slots 158 in the holder tube. The shoulders 134, shown most clearly in FIGS. 15 and 16, engage a tapered distal end of the holder tube 154 causing the pull tabs 130 to be released from the slots 158. As the holder tube 154 is moved further forward, the holder tube causes the second flange to be deployed. The edges of the radial groove 157 are preferably beveled so that the anastomosis device 120 will be able to be removed from the expander tube 156 after the anastomosis device is completely deployed.

One alternative embodiment of the holder tube 154 employs a plurality of flexible fingers which receive the pull tabs 130 of the anastomosis device 120. According to this embodiment each pull tab 130 is received by an independent finger of the holder tube 154. To deploy the second or outer flange of the anastomosis device 120, the flexible fingers flex outward bending the pull tabs 130 outward.

FIGS. 19–22 illustrate the operation of the handle 160 to move the trocar 152, the holder tube 154, and the expander tube 156 with respect to one another to deploy the anastomosis device 120 according to the present invention. The handle 160 includes a grip 170 and a trigger 172 pivotally mounted to the grip at a pivot 174. The trigger 172 includes a finger loop 176 and three contoured cam slots 178, 180, 182 corresponding to the trocar 152, holder tube 154, and expander tube 156, respectively. Each of these tubes has a fitting 184 at a distal end thereof. A pin 186 connected to each of the fittings 184 slides in a corresponding one of the cam slots 178, 180, 182. A fourth cam slot and tube may be added to control deployment of the second flange.

The handle 160 is shown in FIG. 18 in an insertion position in which the trocar 152 extends beyond the holder tube 154 and the expander tube 156 for puncturing of the target vessel wall 32. As the trigger 172 is rotated from the position illustrated in FIG. 19 to the successive positions illustrated in FIGS. 20–22, the pins 186 slide in the cam slots 178, 180, 182 to move the trocar 152, holder tube 154 and expander tube 156.

Figure 19:
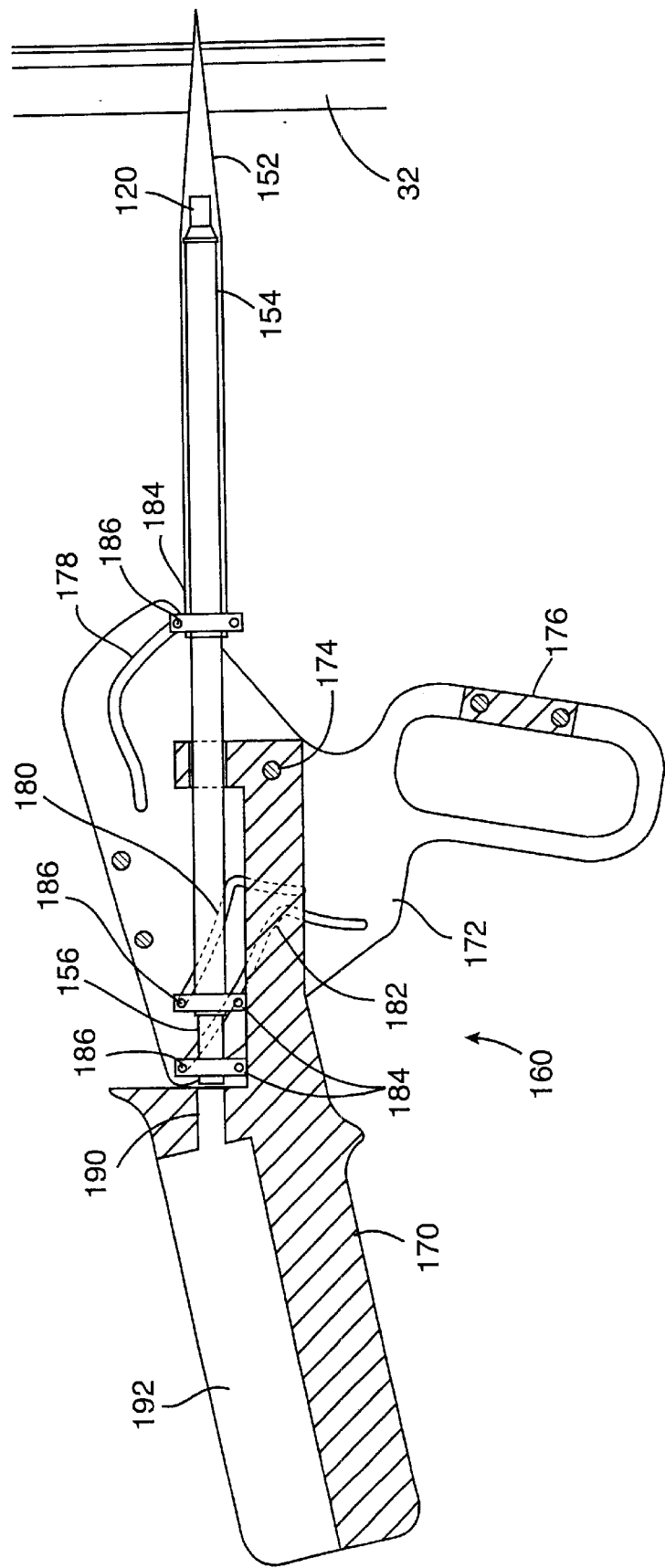
FIG. 19 is a schematic side cross-sectional view of a deployment tool taken along line A—A of FIG. 14, the deployment tool is shown during a vessel puncturing step.

FIG. 20 shows the handle 160 with the trigger 172 rotated approximately 30 degrees from the position of FIG. 19. This rotation moves the holder tube 154 and expander tube 156 forward into the wall of the target vessel 32 spreading the trocar 152. The anastomosis device 120 is now in position for deployment. FIG. 21 shows the trigger 172 rotated approximately 45 degrees with respect to the position of FIG. 19 and the cam slot 182 has caused the expander tube 156 to be advanced within the holder tube 154 to deploy the first flange. The trocar 152 has also been withdrawn.

Figure 22:
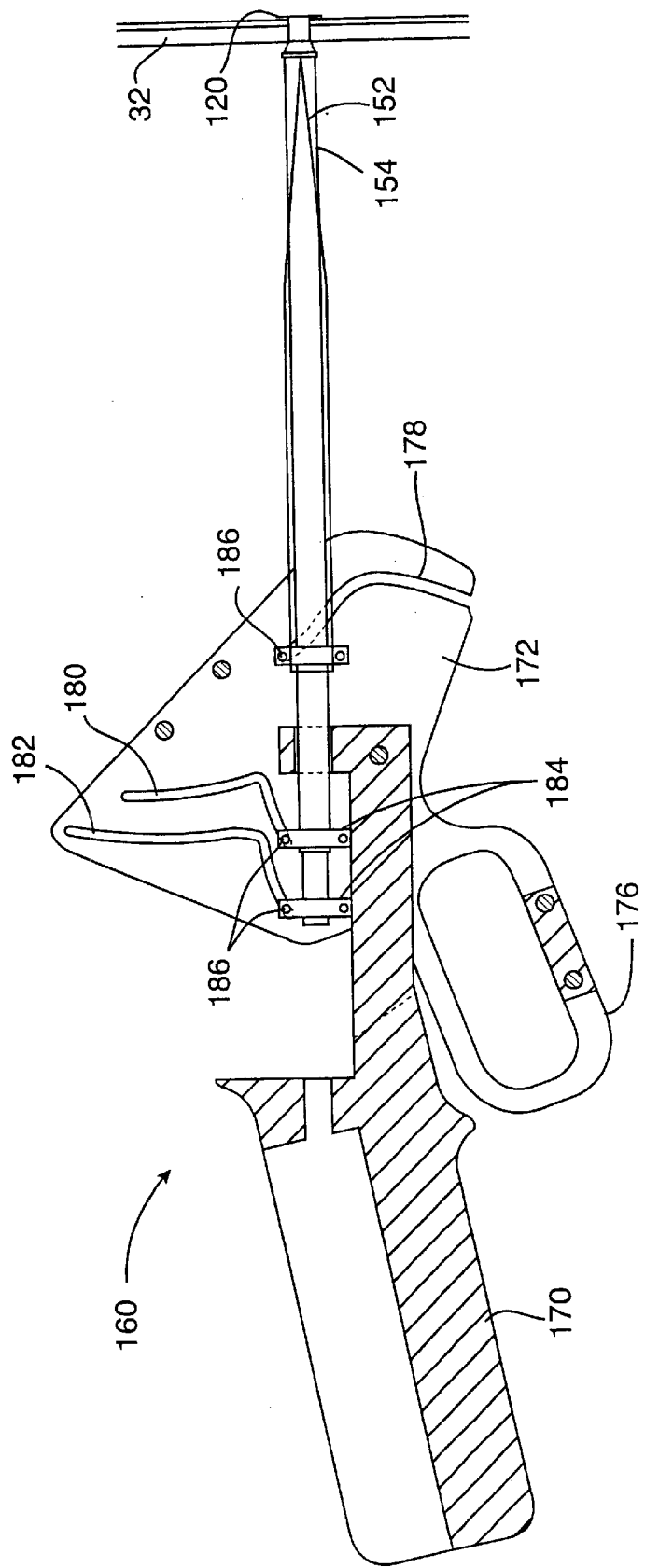
FIG. 22 is a schematic side cross-sectional view of the deployment tool of FIG. 19 shown after the anastomosis device has been fully deployed.

FIG. 22 shows the handle 160 with the trigger 172 pivoted approximately 60 degrees with respect to the position shown in FIG. 19. As shown in FIG. 22, the expander tube 156 has been withdrawn to pull the first flange against the vessel wall 32 and the holder tube 154 is moved forward to deploy the second flange and disengage the holder tube 154 from the anastomosis device 120.

The handle 160 also includes a first channel 188 and a second channel 190 in the grip 170 through which the graft vessel (not shown) may be guided. The grip 170 also includes a cavity 192 for protecting an opposite end of the graft vessel from the attachment end.

Figure 23:
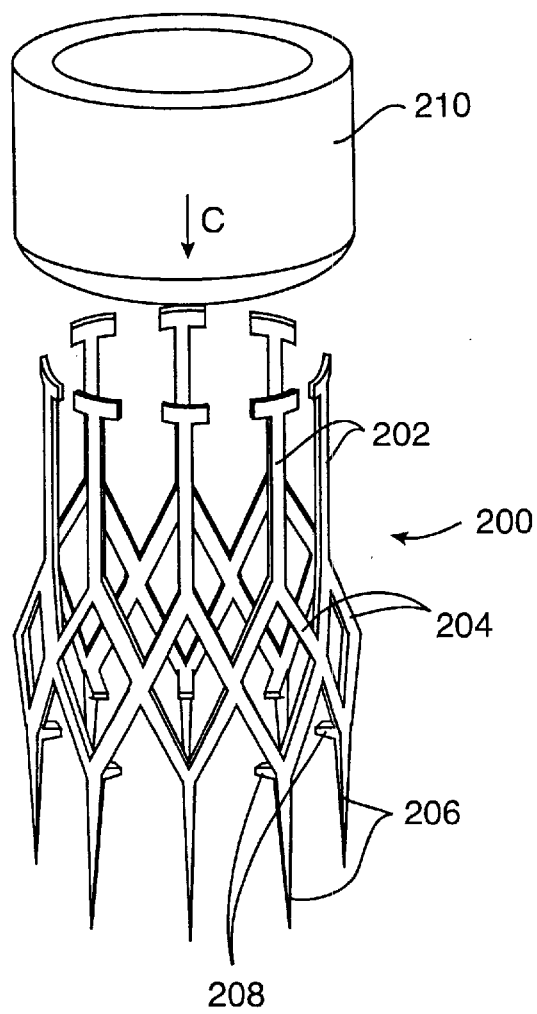
FIG. 23 is a perspective view of a eighth embodiment of an anastomosis device in a configuration prior to use.
Figure 23A:
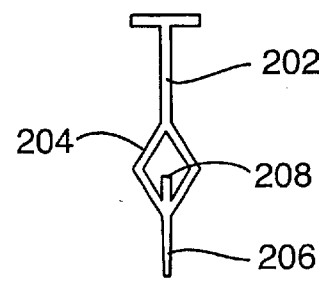
FIG. 23A is a side view of a portion of the anastomosis device of FIG. 23 prior to folding a tab of the device inward.

FIGS. 23–26 illustrate a further alternative embodiment of the anastomosis device according to the present invention. As shown in FIG. 23, an anastomosis device 200 includes a plurality of pull tabs 202, a diamond linkage 204, and a plurality of needles 206. As shown in the detail of FIG. 23A, each of the needles 206 has a tail portion 208 which is bent radially inwardly as shown in FIG. 23 prior to use. In this embodiment, the graft vessel is inserted through the center of the anastomosis device 200 and everted over the needles 206 as in the previous embodiments. The needles 206 puncture the graft vessel and securely retain the graft vessel on the anastomosis device. To deploy the device 200 of FIG. 23, an expander 210 is inserted axially into the device in a direction of the arrow C and engages the tail portions 208 of the needles 206 to fold the needles radially outward. The expander 210 is preferably larger in diameter than an original inner diameter of the device 200 such that the device is expanded during deployment. This expansion will stretch the opening in the target vessel 32 providing a better seal between the graft and target vessels. However, it should be understood that an outer diameter of the expander 210 according to this embodiment can be equal to or smaller than an inner diameter of the device 200 and can bend the needles 206 outward without radially expanding the device.

Figure 24:
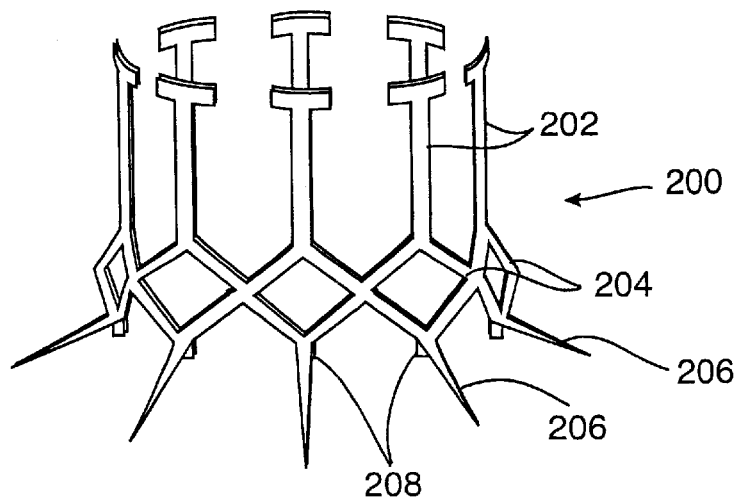
FIG. 24 is a perspective view of the anastomosis device of FIG. 23 in a deployed configuration.

FIG. 24 illustrates the device 200 of FIG. 23 in which the expander has been used to radially expand the device and bend the needles 206 outward. The pull tabs 202 are then folded downward to trap the wall of the target vessel 32 between the needles 206 and the pull tabs.

Figure 25:
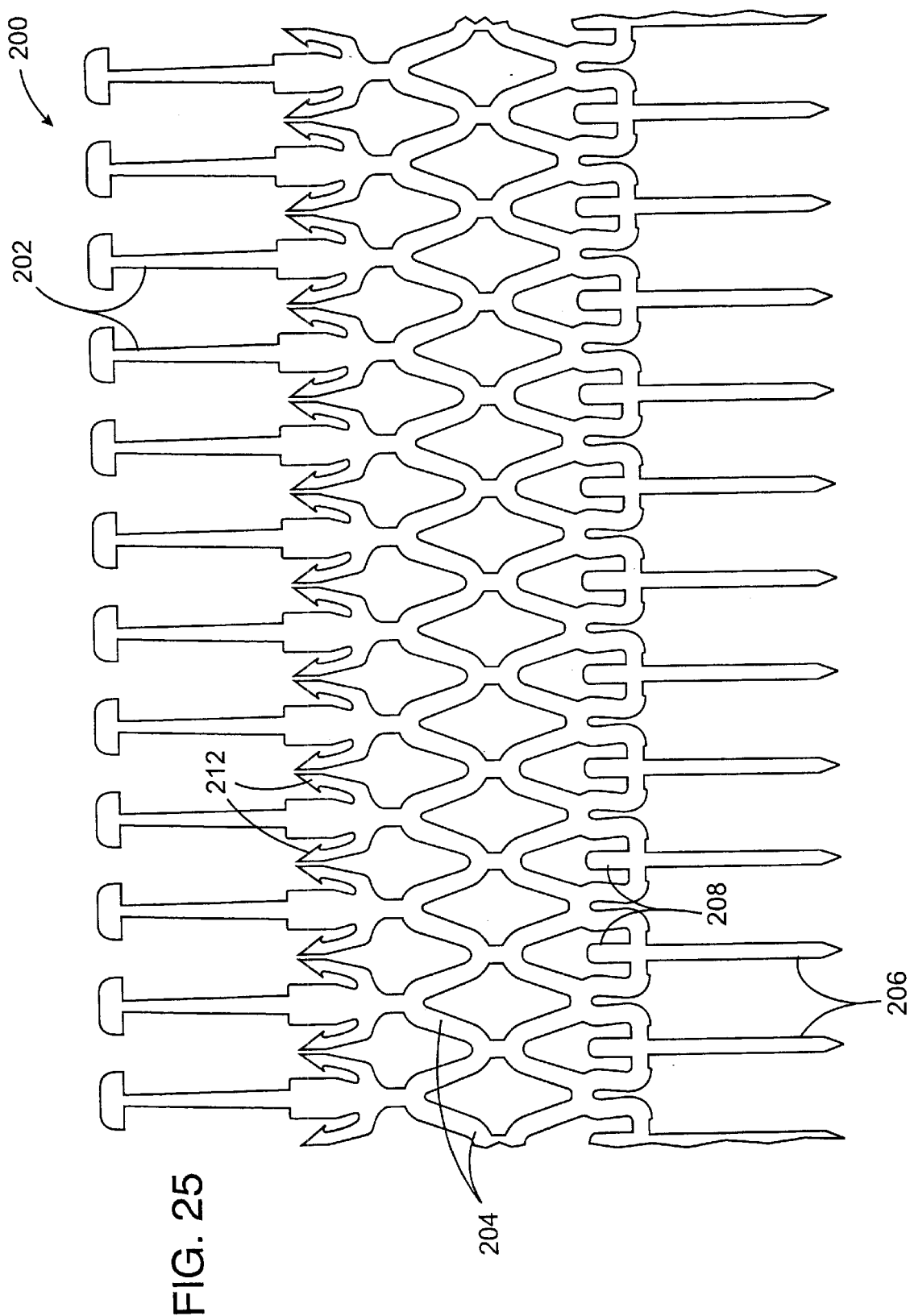
FIG. 25 is a side view of a portion of a ninth embodiment of an anastomosis device which has been laid flat for ease of illustration.
Figure 26:
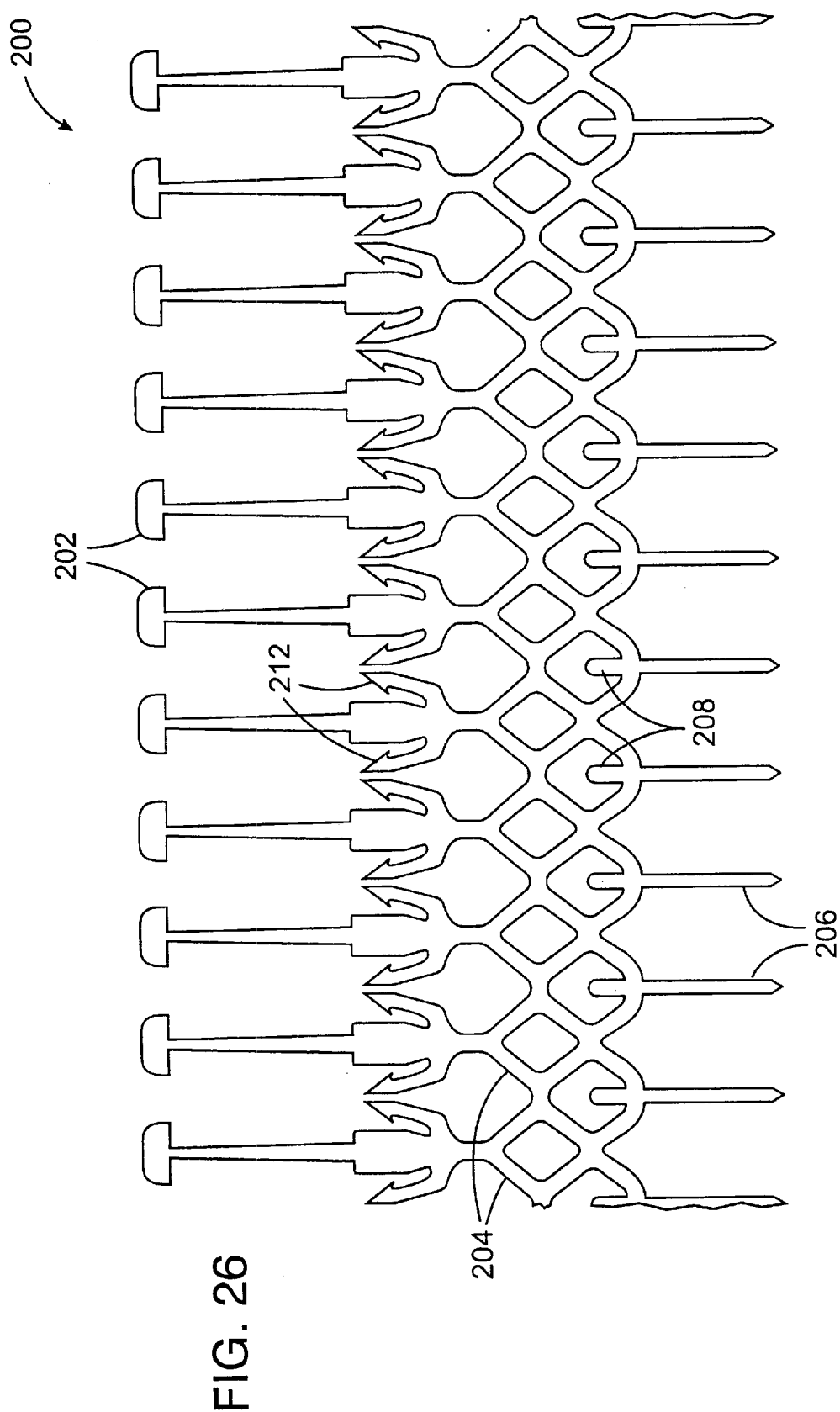
FIG. 26 is a side view of a portion of a tenth embodiment of an anastomosis device which has been laid flat for ease of illustration.

FIGS. 25 and 26 illustrate two modified versions of the embodiment of FIG. 23. The variations of FIGS. 24 and 25 each include pull tabs 202, diamond linkages 204, and needles 206 having tail portions 208 bent inwardly. FIG. 25 and 26 also illustrate horns 212 which help to retain the graft vessel after eversion.

A cantilevered end of each of the axial members may be either rounded as shown in FIGS. 12 and 13 or pointed as shown in FIGS. 1, 2, 5 and 6. The rounded cantilever ends prevent puncturing of the graft vessel while the pointed cantilever ends puncture through the vessel and prevent the vessel from slipping off of the anastomosis device. The puncturing of the vessel also relieves stresses on the vessel which are created when expanding the first flange. Although the pointed cantilever ends may provide more secure retention of the graft vessel, these pointed ends will provide undesirable metal within the bloodstream.

Figure 27:
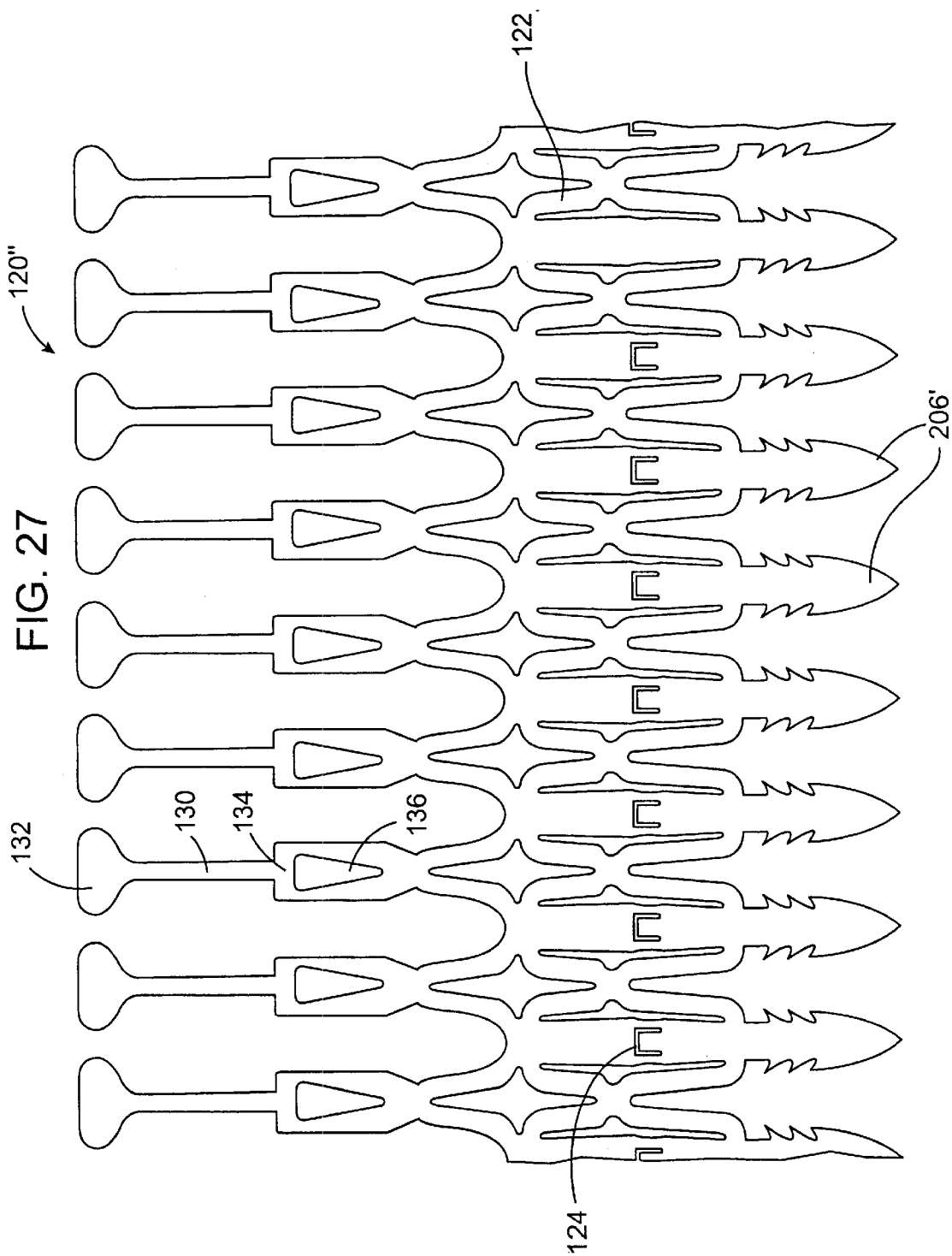
FIG. 27 is a side view of a portion of an eleventh embodiment of an anastomosis device which has been laid flat for ease of illustration.

FIG. 27 illustrates a modified version of the anastomosis device of FIG. 12 in which the anastomosis device 120" includes modified needles 206' with saw tooth edges for grasping tissue of the graft vessel. This version of the anastomosis device 120" also includes backstop hinges 124 and pull tabs 130.

Figure 28:
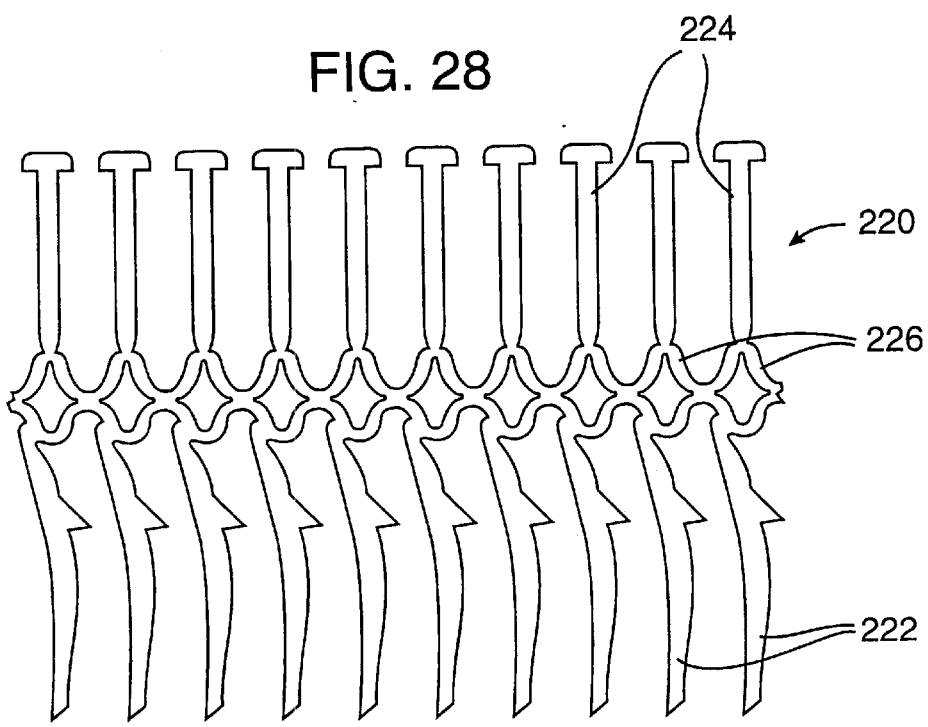
FIG. 28 is a side view of an eleventh embodiment of an anastomosis device which has been laid flat for ease of illustration.
Figure 29:
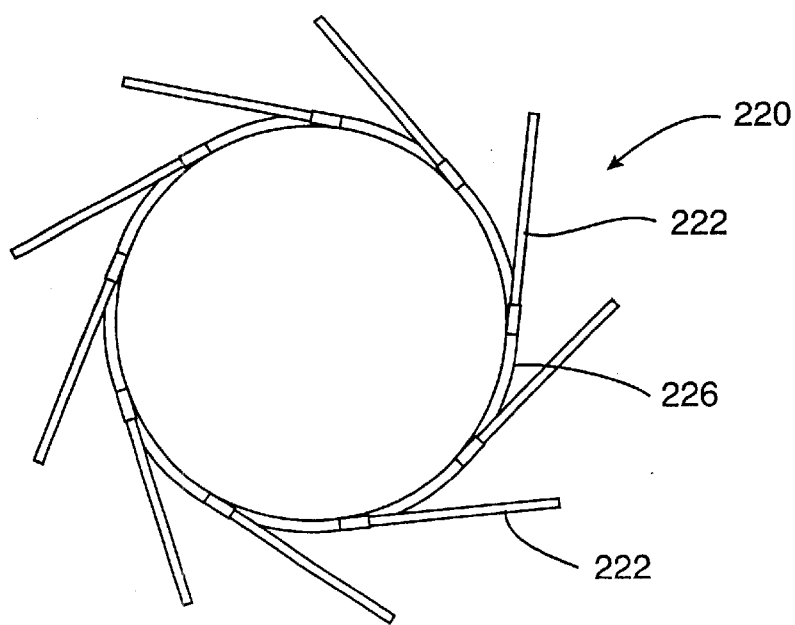
FIG. 29 is a top view of the anastomosis device of FIG. 28 with a flange deployed.

FIGS. 28 and 29 illustrate an alternative embodiment of an anastomosis device 220. Having the first flange formed from a plurality of members 222 which fold out tangentially from a body of the anastomosis device. The device 220 includes pull tabs 224, connected by a diamond linkage 226 to the members 222. As the diamond linkage 226 is expanded in the manner described above with respect to the earlier embodiments, the members 222 fold outward in a direction which is substantially tangential to a body of the expanding device as shown in FIG. 28. The tangentially folded members 222 form the inner flange of the device 220. The pull tabs 224 are then folded downward to form the outer flange. According to this embodiment of the invention, a second flange may also be formed from a plurality of members which fold out tangentially from a body of the anastomosis device.

Each of the anastomosis devices described above are preferably single piece devices which are formed by laser cutting or punching from a tube or sheet of material. The devices may be provided in varying sizes to join vessels of different sizes. The linkages, pull tabs, and other elements which have been discussed above with regard to the various embodiments may be used in varying numbers and arrangements.

The invention has been described as an anastomosis device which is expanded with an expander. The expander may be a tube, a balloon, or any other known expanding device.

Although the invention has been principally discussed with respect to coronary bypass surgery, the anastomosis devices of the present invention may be used in other types of anastomosis procedures. For example, the anastomosis device may be used in femoral-femoral bypass, vascular shunts, subclavian-carotid bypass, organ transplants, and the like.

The anastomosis devices may be made of any known material which can be bent and will retain the bent shape such as stainless steel, nickel titanium alloys, and the like. The hinges or pivot joints which have been discussed above in the various embodiments of the present invention are designed to concentrate the bending at a desired location. For example, the hinges may be formed with a reduced thickness or width, or with openings in order to concentrate the bending in the hinges.

The dimensions of the anastomosis device of the present invention are determined by the dimensions of the blood vessels to be joined. A distance between the two flanges is designed to accommodate the wall thickness of a target vessel which may vary. The anastomosis devices according to the present invention have been illustrated as cylindrical members. However, the devices may also be shaped into oval shapes, football shapes, or other shapes to accommodate smaller target vessels.

While the invention has been described in detail with reference to the preferred embodiments thereof, it will be apparent to one skilled in the art that various changes and modifications can be made and equivalents employed, without departing from the present invention.

What is claimed is:

1. A method of performing anastomosis, comprising:
providing a one-piece tubular anastomosis device;
everting an end of a graft vessel about an end of the anastomosis device;
puncturing a target vessel;
inserting the anastomosis device with everted graft vessel into the puncture in the target vessel;
radially expanding the anastomosis device by advancing an expander into the anastomosis device to cause a portion of the anastomosis device to deform outward forming a first annular flange; and
forming a second annular flange on the anastomosis device to trap a wall of the target vessel between the first and second annular flanges and seal the graft vessel to the target vessel.

2. The method of claim 1, wherein the expander has an outer diameter greater than an inner diameter of the anastomosis device.

3. The method of claim 1, wherein the forming of the second flange results from motion of the expander out of the anastomosis device.

4. The method of claim 3, wherein a groove on the expander catches at least a portion of the anastomosis device to form the second flange.

5. The method of claim 1, wherein the expander is an inflatable balloon.

6. The method of claim 1, wherein the radial expansion of the anastomosis device causes a portion of the device to bend at a plurality of hinges to form the first annular flange.

7. The method of claim 1, wherein the first and second annular flanges each form an angle between about 45 and 100 degrees with an axis of the device.

8. A method of performing anastomosis, comprising
providing a one-piece tubular expandable anastomosis device;
everting the end of a graft vessel about an end of the anastomosis device;
creating an opening in a target vessel;
inserting the anastomosis device with the everted graft vessel into the opening in the target vessel; and
radially expanding the tubular anastomosis device to support tissue surrounding the opening in the target vessel by longitudinally moving an expander relative to the anastomosis device.

9. A method of forming an anastomosis, comprising:
everting one end of a graft vessel about an end of a joining device;
inserting the joining device with the everted first vessel through a wall of a second vessel, said wall having an interior wall surface and an exterior wall surface;
radially expanding the joining device inside the second vessel by advancing an expander into the anastomosis device to form a first protuberance;
seating the first protuberance against the interior wall surface of the second vessel; and
forming a second protuberance in the joining device to thereby retain the wall of the second vessel between the first and second protuberances.

10. The method of claim 9, wherein the joining device comprises a body of elements which form movable linkages including hinges, radially expanding the body causing bending of the hinges to form the first protuberance.

11. The method of claim 10, wherein radially expanding the body causes bending of the hinges to form the second protuberance.

* * * * *